US008372596B2

(12) United States Patent
Kuroda et al.

(10) Patent No.: US 8,372,596 B2
(45) Date of Patent: Feb. 12, 2013

(54) ASBESTOS DETECTION METHOD, ASBESTOS DETECTION AGENT, ASBESTOS DETECTION KIT, METHOD FOR SCREENING CANDIDATE FOR AGENT AIMING AT PREVENTING OR TREATING DISEASE FOR WHICH ASBESTOS IS CAUSATIVE OR WORSENING FACTOR

(75) Inventors: Akio Kuroda, Higashihiroshima (JP); Kazutaka Nomura, Higashihiroshima (JP)

(73) Assignee: National University of Corporation Hiroshima University, Higashihiroshima-Shi (JP)

( * ) Notice: Subject to any disclaimer, the term of this patent is extended or adjusted under 35 U.S.C. 154(b) by 509 days.

(21) Appl. No.: 12/093,316

(22) PCT Filed: Nov. 8, 2006

(86) PCT No.: PCT/JP2006/322279
§ 371 (c)(1),
(2), (4) Date: May 9, 2008

(87) PCT Pub. No.: WO2007/055243
PCT Pub. Date: May 18, 2007

(65) Prior Publication Data
US 2009/0098578 A1    Apr. 16, 2009

(30) Foreign Application Priority Data

Nov. 10, 2005 (JP) .................................. 2005-326502
Jan. 12, 2006 (JP) .................................. 2006-005061
May 15, 2006 (JP) .................................. 2006-135674
Jul. 26, 2006 (JP) .................................. 2006-203983

(51) Int. Cl.
*G01N 33/00*        (2006.01)
(52) U.S. Cl. ......... 435/7.92; 435/7.9; 436/501; 436/518
(58) Field of Classification Search ........................ None
See application file for complete search history.

(56) References Cited

U.S. PATENT DOCUMENTS

| 4,248,854 | A | 2/1981 | Lukens, Jr. | |
|---|---|---|---|---|
| 4,918,022 | A * | 4/1990 | Houk | 436/79 |
| 6,329,209 | B1 | 12/2001 | Wagner et al. | |
| 6,365,418 | B1 | 4/2002 | Wagner et al. | |
| 2003/0022216 | A1 | 1/2003 | Mao et al. | |
| 2004/0048289 | A1* | 3/2004 | Matsunaga et al. | 435/6 |
| 2004/0115721 | A1 | 6/2004 | Mao et al. | |
| 2005/0100675 | A1 | 5/2005 | Mao et al. | |
| 2005/0147758 | A1 | 7/2005 | Mao et al. | |
| 2009/0118142 | A1 | 5/2009 | Kuroda et al. | |
| 2010/0081735 | A1 | 4/2010 | Mao et al. | |
| 2010/0216253 | A1 | 8/2010 | Shiotsuka et al. | |

FOREIGN PATENT DOCUMENTS

| JP | 2002-520618 A | 7/2002 |
|---|---|---|
| JP | 2004-531390 A | 10/2004 |
| JP | 2005-95154 A | 4/2005 |
| JP | 2010-131587 A | 6/2010 |
| WO | WO-2007/055288 A1 | 5/2007 |

OTHER PUBLICATIONS

Grossoehme, Phosphate buffered saline, AFCS Solution Protocol, one page, Dec. 6, 2001.*
Brody et al., Actin-containing microfilaments of Pulmonary Epithelial Cells Provide a Mechanism for Translocating Asbestos to the Interstitium, Chest, 83, May 1983, Supplement pp. 11s-12s.*
Resnick et al., Screted Extracellular Domains of Macrophage Scavernger Receptors Form Elongated Trimers Which Specifically Bind Crocidolite Asbestos, The Journal of Biological Chemistry, vol. 268, No. 5, 1993, pp. 3538-3545.*
Gunning et al., Isolation and Characterization of Full-Lenth cDNA Clones for Human a-, b-, and y-Actin mRNAs: Skeletal but not Cytoplasmic Actins have an Amino-Terminal Cysteine that is subsequently removed, Molecular and Cellular Biology, May 1983, pp. 787-795.*
Verkhusha et al., Expression of recombinant GFP-actin fusion protein in the methylotrophic yeast *Pichia pastoris*, FEMS Yeast, Research 3 (2003) pp. 105-111.*
Kuroda, A. et al. (Feb. 1, 2008). "Detection of Chrysotile Asbestos by Using a Chrysotile-Binding Protein," *Biotechnology and Bioengineering* 99(2):285-289.
Supplementary European Search Report mailed Dec. 1, 2008, for EP Application No. 06823183.6 filed Nov. 8, 2006, 3 pages.
Brody, A. R. et al. (1983). "Interactions of Chrysotile Asbestos with Erythrocyte Membranes," *Environmental Health Perspectives* 51:85-89.
Hennessey, E. S, et al. (1993). "Molecular Genetics of Actin Function," *The Biochemical Journal* 282:657-671.
International Search Report mailed Dec. 12, 2006, for PCT Application No. PCT/JP2006/322279 filed Nov. 8, 2006, 5 pages.
Misra, V. et al. (1983). "Binding of Silicic Acid by Proteins and its Relation to Toxicity of Silicate Dusts," *Journal of Applied Toxicology* 3(3):135-138.
Muller, A. et al. (Mar. 1, 2001). "Involvement of Chemokine Receptors in Breast Cancer Metastasis," *Nature* 410:50-56.
Resnick, D. et al. (Feb. 15, 1993). "Secreted Extracellular Domains of Macrophage Scavenger Receptors Form Elongated Trimers which Specifically Bind Crocidolite Asbestos," *The Journal of Biological Chemistry* 268(5):3538-3545.
Office Action received for Japanese Patent Application No. 2007-544159 mailed on May 8, 2012, 5 Pages. (3 pages of English translation and 2 pages of Office Action), May 8, 2012.

(Continued)

*Primary Examiner* — Gary W Counts
(74) *Attorney, Agent, or Firm* — Morrison & Foerster LLP

(57) ABSTRACT

The present invention provides a prompt and easy asbestos detection method and a method for screening a candidate for an agent aiming at preventing or treating a disease for which asbestos is a causative or worsening factor. It is possible to quickly and easily detect asbestos in a sample by finding a protein capable of binding specifically to asbestos, allowing the protein or a fusion protein of the protein and a reporter protein to bind to asbestos in the sample, and then detecting the protein or the fusion protein having been bound to asbestos. A substance inhibiting the binding of actin to asbestos, which has been found out as a protein capable of binding specifically to asbestos, is a candidate for an agent aiming at preventing or treating a disease for which asbestos is a causative or worsening factor.

5 Claims, 16 Drawing Sheets

OTHER PUBLICATIONS

Ishida et al., "Selective Detection of Airborne Asbestos Fibers Using Protein-Based Fluorescent Probes", Environmental Science & Technology, vol. 44, No. 2, 2010, pp. 755-759.

Office Action received for Japanese Patent Application No. 2007-544184, mailed on Mar. 6, 2012, 6 pages (4 pages of English Translation and 2 pages of Office Action), Mar. 6, 2012.

Funato, T. (Oct. 10, 2005). "Asbestos to Rinsho Kensa," Iryo to Kensa Kiki-Shiyaku 28(5):403-406.

Japanese Office Action mailed Jan. 10, 2012, for Japanese Application No. 2007-544159, 12 pages (including English translation).

Kamiyama, N. (2004). "Chuhishu ni Okeru Sekimen Bakuro Jokyo no Bunsekiho," Pathology and Clinical Medicine 22(7):667-674.

Nishimura, T. (Aug. 3, 2006). "Asbestos Ketsugo Tanpakushitsu o Riyo shita Abestos Kenshutsu Gijutsu Kaihatsu," The Society for Biotechnology, Japan Taikai Koen Yoshishu 58:33.

* cited by examiner

BUILDING MATERIAL 1

BUILDING MATERIAL 2

BUILDING MATERIAL 3

ROCK WOOL

ASBESTOS DETECTION METHOD, ASBESTOS DETECTION AGENT, ASBESTOS DETECTION KIT, METHOD FOR SCREENING CANDIDATE FOR AGENT AIMING AT PREVENTING OR TREATING DISEASE FOR WHICH ASBESTOS IS CAUSATIVE OR WORSENING FACTOR

CROSS REFERENCE TO RELATED APPLICATIONS

This application is a U.S. National Phase patent application of International Application No. PCT/JP2006/322279, with an international filing date of Nov. 8, 2006, which claims priority to Japanese Patent Application No. 326502/2005 filed on Nov. 10, 2005, Japanese Patent Application No. 005061/2006 filed on Jan. 12, 2006, Japanese Patent Application No. 135674/2006 filed on May 15, 2006, and Japanese Patent Application No. 203983/2006 filed on Jul. 26, 2006, all of which are incorporated herein by reference in their entirety.

TECHNICAL FIELD

The present invention relates to a method for detecting asbestos in a sample by using a protein capable of binding specifically to asbestos, an asbestos detection agent containing the protein, an asbestos detection kit including the asbestos detection agent, and a method for screening a candidate for an agent aiming at preventing or treating a disease for which asbestos is a causative or worsening factor, by using the protein.

BACKGROUND ART

Recently, asbestos (fibrous silicate) has become a problem since it has adverse effects on human body. Specifically, a company has disclosed to the public that workers who have been involved in producing asbestos or handling asbestos develop health problems such as lung cancer and mesothelioma at a high incidence rate. In addition, it has been reported that inhalation of asbestos powder dust may cause health problems mainly including asbestosis, lung cancer, and malignant mesothelioma.

Asbestosis is a kind of pulmonary fibrosis (pneumonoconiosis), which is a disease that causes fibrosing lung.

There are many factors that cause the fibrosing lung, including other mineral powder dust. However, pulmonary fibrosis caused by exposure to asbestos is classified especially into asbestosis. Lung cancer is developed mainly by physical stimulation of asbestos fibers taken up in alveoli of the lung. The level of carcinogenicity of asbestos varies depending upon the type, thickness, and length, of asbestos. Malignant mesothelioma is a malignant tumor of a pleura surrounding lung, peritoneum surrounding organs such as liver and stomach, and the like part.

Examples of asbestos include chrysotile (white asbestos), crocidolite (blue asbestos), amosite (brown asbestos), anthophylite, toremolite, and actinolite. More than 90% of the use of asbestos is for building materials. In other examples, asbestos is used for sealing materials for chemical plant setup, and industrial products such as friction materials. Manufacture and handling of building materials, friction materials, and adhesives containing asbestos have been banned since Oct. 1, 2004. However, there were circumstances where a large amount of asbestos was used in the past, and asbestos has remained in many buildings.

Detection of asbestos is performed by the following method. That is, for the detection of asbestos in the air, asbestos is trapped by a filter when the air is taken in by a pump, and the filter is subjected to achromatization by using acetone to observe the filter through a phase microscope. For the detection of asbestos in building material, a sample is collected by appropriate amount from a building material to be analyzed, and the collected sample is subjected to grinding, pulverization, heating, and/or other treatments according to the form of the building material and the state of a substance that coexists with the building material to prepare a sample to be analyzed. Next, the sample to be analyzed is subjected to qualitative analysis by disperse dyeing analysis method through a phase microscope and qualitative analysis by X-ray diffraction analysis so as to determine whether the sample contains asbestos. The sample which has been identified as the one containing asbestos is treated with formic acid to prepare a sample to be subjected to quantitative analysis. Then, the sample is subjected to quantitative analysis by X-ray diffraction analysis method that uses base standard absorption correction method to find the amount of asbestos contained and calculate the percentage of asbestos content (see Non-Patent Documents 1 and 2).

However, observation through a phase microscope requires advanced skills and requires a considerable time. Therefore, it is difficult to perform many operations at the same time. Besides, X-ray analyzer is very expensive and cannot be used easily by anyone.

[Non-Patent Document 1]

Working Environment measurement Series No. 3: Manual of Fibrous Substance Measurement, Japan Association for Working Environment Measurement, Jul. 28, 2004

[Non-Patent Document 2]

Method of Analyzing Asbestos Content in Building Material, *Kiankahatsu* (Ministry of Health, Labour, and Welfare, Labour Standards Bureau, Industrial Safety and Health Department, Chemical Hazards Control Division) No. 0622001 号, Jun. 22, 2005

DISCLOSURE OF INVENTION

As described previously, it is revealed that asbestos is a causative or worsening factor. However, mechanism of induction of the above diseases by asbestos has been hardly clarified, and research on the treatment of diseases induced by asbestos has hardly proceeded. Under such circumstances, there has been a growing demand from society as a whole for the development of a method by which asbestos can be detected promptly and easily.

If a protein capable of binding specifically to asbestos is found out, it is very useful for prompt and easy asbestos detection, and is very significant in the field of public sanitation. In addition, if it was found out that a protein capable of binding specifically to asbestos which protein exists in a living body, particularly respiratory organs such as lung of a mammal, such finding makes a significant contribution to the clarification of the mechanism of induction of the diseases by asbestos, and it is expected that inhibition of binding of protein to asbestos leads to prevention or treatment for diseases induced by asbestos.

However, the existence of a protein capable of binding specifically to asbestos was not reported in the past.

The present invention has been attained in view of the above problems, and an object of the present invention is to find out a protein capable of binding specifically to asbestos, realize a prompt and easy asbestos detection method, find out a protein capable of binding specifically to asbestos in respiratory organs of a mammal, and provide a method for screening a candidate for an agent aiming at preventing or treating a disease for which asbestos is a causative or worsening factor.

In order to solve the above problems, the inventors of the present invention found out a protein capable of binding to asbestos from among various kinds of bacterium-derived proteins, found out that it is possible to promptly and easily detect asbestos by using a fusion protein of such a protein and a reporter protein. In addition, the inventors of the present invention accomplished the present invention by finding out a protein capable of binding to asbestos from among proteins that exist in mouse lung, and identifying the protein as actin.

That is, an asbestos detection method according to the present invention includes: the step of bringing a protein capable of binding to asbestos in a solution containing at least 0.1 M or more sodium chloride into contact with asbestos in a sample; and the step of detecting the protein binding to the asbestos.

Further, an asbestos detection method according to the present invention includes: the step of obtaining a fusion protein of (i) a protein capable of binding to asbestos in a solution containing at least 0.1 M or more sodium chloride and (ii) a reporter protein; the step of bringing the obtained fusion protein into contact with asbestos in a sample; and the step of detecting the fusion protein binding to the asbestos.

An asbestos detection agent according to the present invention contains a protein capable of binding to asbestos in a solution containing at least 0.1 M or more sodium chloride.

Further, an asbestos detection agent according to the present invention contains a fusion protein of (i) a protein capable of binding to asbestos in a solution containing at least 0.1 M or more sodium chloride and (ii) a reporter protein.

The asbestos detection method and the asbestos detection agent according to the present invention are preferably such that the protein capable of biding to asbestos in the solution containing at least 0.1 M or more sodium chloride is at least one type of protein selected from: a protein with an amino acid sequence represented by SEQ ID NO: 1, 3, 5, 7, 9, 11, 13, 15, 17, 19, 21, 23, or 25; and a protein with amino acid sequence having deletion, substitution, or addition of one or several amino acids in an amino acid sequence represented by SEQ ID NO: 1, 3, 5, 7, 9, 11, 13, 15, 17, 19, 21, 23, and 25.

The asbestos detection method and the asbestos detection agent according to the present invention are preferably such that the protein capable of binding to asbestos in the solution containing at least 0.1 M or more sodium chloride is actin.

The asbestos detection method and the asbestos detection agent according to the present invention are preferably such that the reporter protein is a protein selected form fluorescent protein, luciferase, alkaline phosphatase, beta galactosidase, diaphorase, and peroxidase.

An asbestos detection kit according to the present invention includes the asbestos detection agent according to the present invention.

A screening method according to the present invention is a screening method for screening a candidate for an agent aiming at preventing or treating a disease for which asbestos is a causative or worsening factor, the method including: the step of bringing a test substance, asbestos, and actin into contact with each other in a solution containing at least 0.1 M or more sodium chloride; and the step of measuring binding level of the asbestos and the actin in the solution.

With the asbestos detection method and the asbestos detection agent according to the present invention, it is possible to promptly and easily detect the presence or absence of asbestos in a sample. By using a biological sample, the present invention can be applied to diagnosis for asbestos-related health problems.

With the screening method according to the present invention, it is possible to promptly and efficiently screen a candidate for an agent aiming at preventing or treating a disease for which asbestos is a causative or worsening factor.

Additional objects, features, and strengths of the present invention will be made clear by the description below. Further, the advantages of the present invention will be evident from the following explanation in reference to the drawings.

BRIEF DESCRIPTION OF DRAWINGS

FIG. 4(*b*) is an electrophoretogram showing that DksA-AP fusion protein tightly binds to asbestos (chrysotile).

BEST MODE FOR CARRYING OUT THE INVENTION

Figure 1:
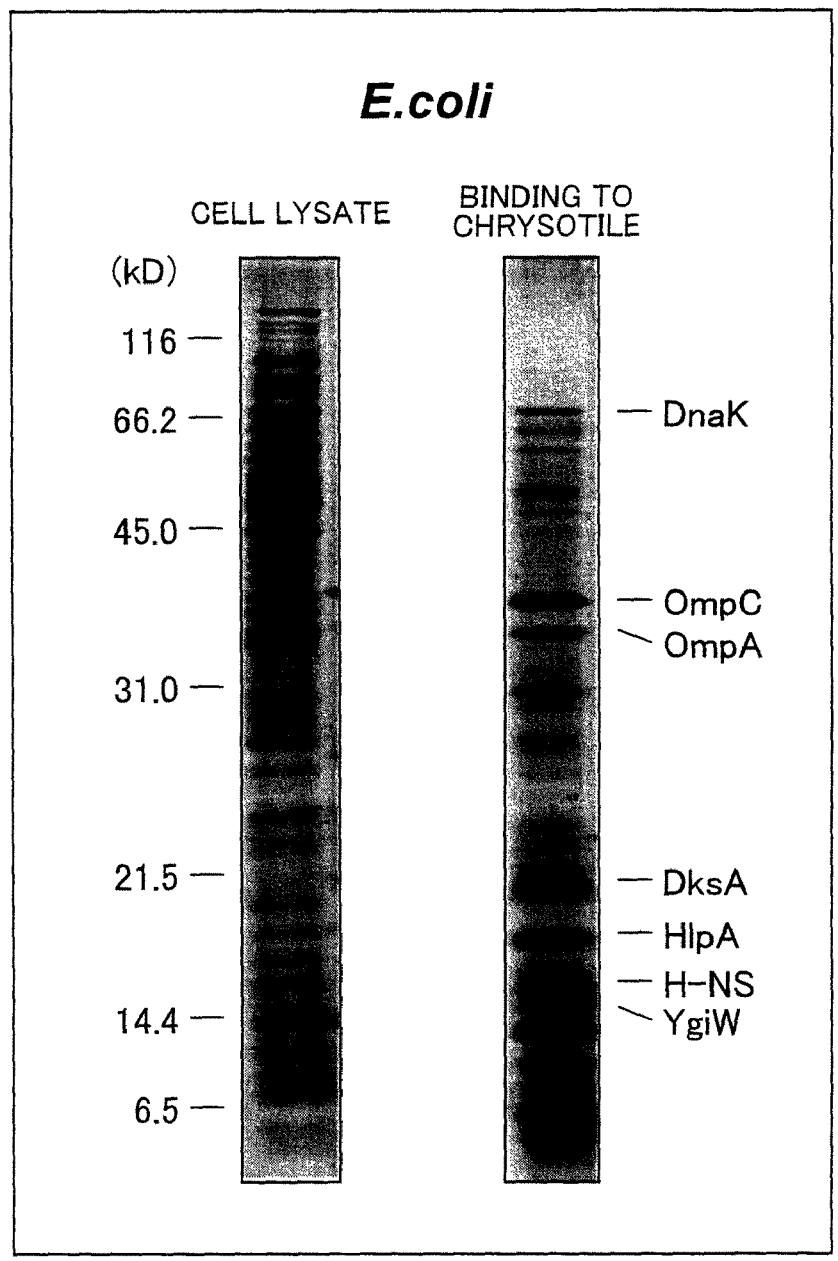
FIG. 1 is an electrophoretogram showing that an asbestos (chrysotile) binding protein was obtained from a cell lysate of *Escherichia coli* K12.

[Obtaining and Identification of Protein Binding to Asbestos]

A protein used in the present invention is a protein capable of binding to asbestos in a solution containing at least 0.1 M or more sodium chloride. The "protein capable of binding to asbestos in a solution containing at least 0.1 M or more sodium chloride" is herein referred to as "protein binding to asbestos". The protein may be derived from, but are not limited to, bacterium, yeast, plant, animal, or any living organisms.

The type of the asbestos is not limited. The protein used in the present invention has only to be a protein capable of binding to any type of asbestos in a solution containing at least 0.1 M or more sodium chloride. For example, the "protein binding to asbestos" includes a protein capable of binding to chrysotile (white asbestos), not to crocidolite (blue asbestos), in a solution containing at least 0.1 M or more sodium chloride.

The word "protein" herein is used interchangeably with "polypeptide" or "peptide". The "protein" includes a fragment of a protein. Further, the "protein" includes a fusion protein. The "fusion protein" is a protein in which part (fragment) or whole of at least two heteroproteins are bound to each other.

For example, the protein binding to asbestos which protein used in the present invention can be obtained by the following method. However, this is not the only possibility. The protein capable of binding to asbestos in a solution containing at least 0.1 M or more sodium chloride can be suitably used in the present invention.

That is, the protein binding to asbestos which protein used in the present invention can be obtained by adding asbestos to a solution containing one or more types of proteins, collecting the asbestos, washing the collected asbestos in a solution containing at least 0.1 M or more sodium chloride, and then isolating the protein(s) binding to the asbestos even after the washing.

As the solution containing at least one or more types of proteins (hereinafter referred to as "protein solution"), for example, a cell lysate can be suitably used. For example, a random peptide library derived from a phage library or synthesized peptide library can be suitably used. However, this is not the only possibility. The protein solution may contain substances other than a protein.

The protein solution may be prepared by a known method that is appropriately selected according to a material as used. For example, the cell lysate can be prepared by a method of physically disrupting cells by means of a homogenizer, ultrasonic waves, or the like, a method of crushing cells by using an enzyme or a surface activating agent, a method of disrupting cells by a combined use of enzyme or a surface activating agent with a physical method, or other method.

The amount of asbestos to be added is not particularly limited. For example, the inventors of the present invention added 5 mg of asbestos (chrysotile, amosite or crocidolite) to 1 ml of bacterial-derived cell lysate (see Examples 1 and 3). Further, the inventors of the present invention added 5 mg of asbestos (chrysotile) to 0.6 ml of mouse lung-derived cell crushing solution (see Example 2).

After the addition of asbestos to the protein solution, it is preferable to sufficiently mix a mixture solution of the protein and the asbestos. Mixture conditions are not particularly limited. For example, the mixture solution is mixed by inversion at 4° C. for 15 to 30 minutes.

The collection of the asbestos can be performed, for example, by centrifuging the mixture solution at such revolutions that allow the asbestos to precipitate, and then removing a supernatant from the mixture solution. Besides, the collection of the asbestos can be performed by filtering the mixture solution through a filter having an appropriate pore size. However, these methods are not the only possibility. By the collection operation, it is possible to remove a protein which does not bind to asbestos.

The washing is performed to remove a protein binding non-specifically to asbestos. The washing is performed, for example, by a method of adding a solution containing at least 0.1 M or more sodium chloride to the asbestos collected as above, sufficiently mixing the mixture solution by pipetting or the like, and then performing centrifugation and filtering as in the above case. Repeating this operation several times enhances the washing effect. Further, preparation of the protein solution by using a solution containing at least 0.1 M or more sodium chloride makes it possible to enhance the washing effect (effect of removing non-specific binding).

A washing solution is not particularly limited as long as it contains at least 0.1 M or more sodium chloride. However, the washing solution is preferably a buffer solution having near neutral pH. The "solution containing at least 0.1 M or more sodium chloride" is a solution excluding a sodium chloride concentration of below 0.1 M at which many proteins weakly bind non-specifically to asbestos. The protein binding to asbestos weakly can bind to inorganic substances other than asbestos at a sodium chloride concentration of below 0.1 M. The use of the "solution containing at least 0.1 M or more sodium chloride" enables exclusion of adsorption caused by such weak binding, thus enhancing specificity.

The protein binding to asbestos which protein is used in the present invention has only to be a protein capable of binding to asbestos even when washed with the solution containing at least 0.1 M sodium chloride. However, with a washing solution containing a high sodium chloride concentration, it is possible to obtain a protein tightly binding to asbestos. Therefore, it is preferable to use a solution containing sodium chloride with a concentration higher than 0.1 M so as to obtain a protein binding to asbestos. Further, it is possible to obtain a protein exhibiting a higher binding specificity by adding a surface activating agent to the washing solution.

In order to obtain a bacteria-derived protein binding to asbestos, the inventors of the present invention used, as a washing buffer solution, 25 mM Tris-HCl buffer solution (pH 7.5 or pH 8.0) containing 0.1 M or 1M sodium chloride and 0.5% polyoxyethylene sorbitan monolaurate (product name: Tween 20®) (see Examples 1 and 3). Furthermore, in order to obtain a mouse lung-derived protein binding to asbestos, the inventors of the present invention used, as a washing buffer solution, 25 mM Tris-HCl buffer solution (pH 8.0) containing 0.5 M or 1M sodium chloride and 0.5% polyoxyethylene sorbitan monolaurate (product name: Tween 20®) (see Example 2).

Examples of a method of releasing an asbestos binding protein from asbestos include, but are not limited to, a method of using a surface activating agent such as dodecyl sodium sulfate, a method of decreasing pH, and a method of increasing salt concentration in a solution (increasing a sodium chloride concentration to a concentration of approximately 2M). The inventors of the present invention used a solution containing 1% dodecyl sodium sulfate and 2% mercaptoethanol (see Examples).

Identification of the thus obtained protein binding to asbestos can be performed by a known method. For example, a protein released from asbestos as above is separated by polyacrylamide gel electrophoresis, and transferred on a polyvinylidene difluoride (PVDF) film. The film is stained with coomassie brilliant blue, and thereafter a band of a target protein is cut out. A tryptic digest of the protein in the cut band is analyzed by matrix-assisted laser desorption/ionization time-of-flight mass spectrometer (MALDI-TOF-MS), and the target protein is identified by peptide mass fingerprint analysis. As a result, it is possible to obtain an amino acid sequence of the target protein from a known protein database. For example, it is possible to determine an amino acid sequence by using an automatic peptide sequencer.

Determination of an amino acid sequence enables obtaining of a base sequence of a gene encoding the target protein from a known gene database, for example. In another example, a DNA fragment encoding the target protein is cloned with a primer or a probe designed on the basis of the amino acid sequence of the target protein. Thus, it is possible to determine a base sequence of the DNA fragment by using a DNA sequencer.

A protein binding to asbestos which protein can be suitably used in the present invention can be a protein having an amino acid sequence represented by SEQ ID NO: 1, 3, 5, 7, 9, 11, 13, 15, 17, 19, 21, 23, or 25. The inventors of the present invention identified these proteins as proteins binding to asbestos. Among these proteins, the protein having an amino acid sequence represented by SEQ ID NO: 3 and the protein having an amino acid sequence represented by SEQ ID NO: 5 were confirmed to bind to all of the following asbestos, chrysotile (white asbestos), amosite (blue asbestos), and crocidolite (brown asbestos). The inventors of the present invention found out for the first time that these proteins, which are all known proteins, are capable of binding to asbestos. The protein having an amino acid sequence represented by SEQ ID NO: 11 has specificity such that it binds to chrysotile, not to amosite, crocidolite, and silica which is similar to asbestos. Therefore, the protein having an amino acid sequence represented by SEQ ID NO: 11 can be suitably used in the present invention.

Also, the following protein can be suitably used in the present invention. That is, a protein with an amino acid sequence having deletion, substitution, or addition of one or several amino acids in an amino acid sequence represented by SEQ ID NO: 1, 3, 5, 7, 9, 11, 13, 15, 17, 19, 21, 23, or 25, the protein capable of binding to asbestos in a solution containing at least 0.1 M or more sodium chloride.

The wording "deletion, substitution, or addition of one or several amino acids" means deletion, substitution, or addition of amino acids the number of which is the number of amino acids that can be deleted, substituted, or added by a known mutant peptide producing method such as a site-specific mutagenesis (preferably not more than 10, more preferably not more than 7, and further preferably not more than 5). Such a mutant protein is not limited to a protein that is artificially mutated by a known mutant polypeptide producing method, and it may be obtained by isolating and purifying naturally occurring proteins.

It is well known in the art that some of the amino acids in the amino acid sequence of a protein can easily be modified without significantly affecting the structure or function of the protein. It is also known that such a mutant with no significant structural or functional change occurs not only in artificially modified proteins but in nature as well.

The mutant preferably includes substitution, deletion, or addition of amino acid, which may be conservative or non-conservative. Silent substitution, silent addition, and silent deletion are preferable, and conservative substitution is particularly preferable. Neither of these modifications changes the polypeptide activities as described in the present invention.

Representative examples of conservative substitution include: substitution of one of aliphatic amino acids Ala, Val, Leu, and Ile with another amino acid; exchange of hydroxyl residues Ser and Thr; exchange of acidic residues Asp and Glu; substitution between amide residues Asn and Gln; exchange of basic residues Lys and Arg; and substitution between aromatic residues Phe and Tyr.

The protein binding to asbestos according to the present invention may include an additional peptide. An example of an additional peptide is polyarginine tag (Arg-tag), polyhistidine tag (His-tag), or an epitope-labeled peptide such as Myc or Flag.

The protein binding to asbestos according to the present invention can be produced by culturing cells as a supply source of the protein, and isolating and purifying the protein from the cell. Also, the protein binding to asbestos according to the present invention can be produced by constructing a recombinant expression vector by a known genetic engineering technique, and introducing the recombinant expression vector into an appropriate host cell to express a recombinant protein.

For convenience of explanation, the above protein binding to asbestos according to the present invention is hereinafter referred to as "asbestos binding protein" if necessary.

[Asbestos Detection Method]

An embodiment of an asbestos detection method according to the present invention includes: a step of bringing the protein capable of binding to asbestos in a solution containing at least 0.1 M or more sodium chloride (asbestos binding protein) into contact with asbestos in a sample; and a step of detecting the protein binding to asbestos (asbestos binding protein). Note that the asbestos detection method according to the present invention may include step(s) other than the above steps, and details of the other step(s) are not limited.

A sample applied to the method of the present invention may be anything as long as it contains asbestos. A form of the sample is not particularly limited, and the sample may be in the form of a liquid, a solid, a grain, a powder, a fluid, a tissue section, or in other form.

In the step of bringing the protein capable of binding to asbestos in a solution containing at least 0.1 M or more sodium chloride (asbestos binding protein) into contact with asbestos in a sample, an asbestos binding protein solution is added to the sample, or the sample is added to the asbestos binding protein solution. In order to make the asbestos in the sample sufficiently bind to the asbestos binding protein, it is preferable to incubate them at a temperature in the range from 4° C. to room temperature for approximately 5 to 30 minutes. However, incubation conditions are not limited to this.

Note that the wording "bringing the protein capable of binding to asbestos in a solution containing at least 0.1 M or more sodium chloride (asbestos binding protein) into contact with asbestos in a sample" does not intend to mean that the asbestos in the sample and the asbestos binding protein are brought into contact with each other in the solution containing at least 0.1 M or more sodium chloride, but intends to mean that an asbestos binding protein having the capability of binding to asbestos in the solution containing at least 0.1 M or more sodium chloride, i.e. the capability of binding to asbestos even when washed in the solution containing at least 0.1 M or more sodium chloride, is brought into contact with the asbestos in the sample. Therefore, the asbestos binding protein and the asbestos in the sample may contact with each other under any conditions.

At the subsequent stage to the above steps, it is preferable to provide a step for removing a protein that does not bind to the asbestos in the sample. For example, the step can be performed by a method of removing a protein released by centrifugation or filtering, a method of washing the surface of the sample with water, or other method.

In the step of detecting an asbestos binding protein capable of binding to asbestos, the asbestos binding protein can be detected by using a known method. For example, it is possible to immunochemically detect the asbestos binding protein by using an antibody capable of binding specifically to the asbestos binding protein as used. Specifically, it is possible to detect the asbestos binding protein by ELISA method or other method. Further, the asbestos binding protein may be a modified protein. For example, it is possible to detect target asbestos by fluorescence detection using an asbestos binding protein labeled with a fluorescent material such as Cy3, Cy5, or fluorescein. Note that what the asbestos binding protein is labeled with is not limited to fluorescence.

Another embodiment of the method of detecting asbestos in a sample according to the present invention includes: a step of obtaining a fusion protein composed of (i) a protein capable of binding to asbestos in a solution containing at least 0.1 M or more sodium chloride (asbestos binding protein) and (ii) a reporter protein; a step of bringing the obtained fusion protein into contact with asbestos in a sample; and a step of detecting the fusion protein binding to asbestos. Note that a step(s) other than the above steps may be provided, and details of the other step(s) are not limited.

In this case, the reporter protein is a protein that is capable of maintaining its reporter function even when fused with an asbestos binding protein to form a fusion protein. Particularly, the reporter protein is preferably a protein by which its reporter function can be easily detected. Examples of the reporter protein include a fluorescent protein and enzyme. More specifically, examples of the reporter protein include a green fluorescent protein, luciferase, alkaline phosphatase, beta galactosidase, diaphorase, and peroxidase.

In the step of obtaining the fusion protein of the asbestos binding protein and the reporter protein, the fusion protein is obtained as a recombinant protein by using a known genetic engineering technique. That is, it is possible to use a method of artificially coupling a gene encoding the asbestos binding protein with a gene encoding the reporter protein to produce a fusion gene (hybrid gene), inserting the fusion gene downstream of a promoter of an expression vector, and introducing the expression vector into a host cell such as *Escherichia coli* to express the fusion gene. Specific examples of methods for construction of the expression vector for the fusion protein and expression and purification of the fusion protein will be described in Examples below.

The step of bringing the fusion protein into contact with the asbestos in the sample can be performed according to the foregoing step, i.e. the step of bringing a protein capable of binding to asbestos in a solution containing at least 0.1 M or more sodium chloride (asbestos binding protein) into contact with asbestos in a sample. At the subsequent stage to this step, it is preferable to provide a step for removing a protein that does not bind to the asbestos in the sample. The removing step can also be performed according to the foregoing step.

In the step of detecting a fusion protein binding to the asbestos, the function of the reporter protein portion in the fusion protein is detected.

For example, in a case where GFP is used as the reporter protein portion of the fusion protein, the presence or absence of particles emitting green fluorescence is observed by using a fluorescence microscope. Further, in a case where luciferase is used for the reporter protein, luciferin, as a substrate, and ATP are added so that the amount of chemiluminescence is measured by using a luminometer.

In a case where an enzyme such as alkaline phosphatase, beta galactosidase, diaphorase, and peroxidase is used for the reporter protein, the amount of fluorescence or the amount of coloring caused with the use of fluorescent substrate or chromogenic substrate is measured by using a fluorophotometer or a spectrophotometer. In a case where chromogenic substrate is used, detection by visual observation is also possible.

In an asbestos detection method according to the present invention, an asbestos binding protein is preferably a protein with an amino acid sequence represented by SEQ ID NO: 1, 3, 5, 7, 9, 11, 13, 15, 17, 19, 21, 23, or 25, and at least one type of protein selected from proteins with an amino acid sequence having deletion, substitution, or addition of one or several amino acids in an amino acid sequence represented by SEQ ID NO: 1, 3, 5, 7, 9, 11, 13, 15, 17, 19, 21, 23, or 25. The protein with an amino acid sequence represented by SEQ ID NO: 1, 3, 5, 7, 9, 11, 13, 15, 17, 19, 21, 23, or 25 is identified as a protein capable of binding to asbestos by the inventors.

The protein with an amino acid sequence represented by SEQ ID NO: 19 is a protein capable of binding to asbestos, and is an alkaline phosphatase used as the reporter protein. Therefore, it is preferable to use alkaline phosphatase as the reporter protein of the fusion protein for use in asbestos detection.

The protein with an amino acid sequence represented by SEQ ID NO: 21 or 23 is actin that was found out as a protein binding to asbestos among proteins in a mouse lung tissue. Specifically, the protein with an amino acid sequence represented by SEQ ID NO: 21 is γ-actin derived from mouse cytoplasm. The protein with an amino acid sequence represented by SEQ ID NO: 23 is β-actin derived from mouse cytoplasm.

Actin is a protein existing in all eucaryotic cells, and the amount of actin is the largest among all proteins existing in the eucaryotic cells (5% out of all proteins, 20% out of the entire weight of skeletal muscle cells in a vertebrate). Actin plays an essential role in living and serves as a basic constituent element of cytoskeleton. In addition, actin is utilized in the activities involving in motion such as muscle contraction, karyokinesis, protoplasmic streaming, endocytosis, and exocytosis. Actin exists as F-actin (fibrous actin) in a muscle, and a complex (actomyosin) of actin and myosin is formed, thereby producing contractive force.

As one of the big features of actin, it is known that the structure of actin is conserved with highly excellent conditions in all organisms. For example, human actin has 90% amino acid sequence identity with yeast actin, and human actin has approximately 60% amino acid sequence identity even with protozoan actin, which has the lowest homology to mammalian actin. At least 6 types of actins exist in mammals, whereas one type of actin exists in yeast. α-actin exists in muscle cells, and β-actin and γ-actin exist in nonmuscle cells. Actin is obtained from actin filament as a result of treatment of dry muscle powder with a dilute saline solution.

Human, mouse, rat, rabbit, and chicken are identical in amino acid sequence of skeletal muscle α-actin. Human, mouse, rat, cow, and chicken are identical in amino acid sequence of cytoplasmic β-actin (for example, see Hennessey E S, Drummond D R, Sparrow J C. Molecular genetics of actin function. Biochem J. 282, 657-671, 1993). As to γ-actin, at least human and mouse are identical in its amino acid sequence.

Note that an amino acid sequence of human γ-actin (ACCESSION: NM_001614) and a base sequence of a gene encoding human γ-actin were represented by SEQ ID NO: 27 and 28, respectively. An amino acid sequence of human β-actin (ACCESSION: NM_001101) and a base sequence of a gene encoding human β-actin were represented by SEQ ID NO: 29 and 3034, respectively.

Therefore, it can be easily supposed that actin usable for asbestos detection is not limited to the actin with an amino acid sequence represented by SEQ ID NO: 21 or 23, and all of the actins capable of binding to asbestos can be used in the asbestos detection method according to the present invention. An amino acid sequence of actin in a mammal including human is identical with or highly homologous to the above amino acid sequence represented by SEQ ID NO: 21 or 23. Therefore, mammalian actin is suitable for use in asbestos detection. In addition, mammalian actin (e.g. skeletal muscle-derived actin of cow, pig, and rabbit) is suitable, considering that the mammalian actin is easily available since it has been commercialized as a reagent.

Further, phalloidin is known as a protein capable of binding specifically to F-actin (fibrous actin). Phalloidin is a cycric peptide consisting of seven amino acids separated as toxic component of Amanita phalloides, and is collectively called phallotoxins, including similar compounds whose structure was determined after phalloidin had been found out. Phalloidin binds specifically to actins of various species including plants and animals. Therefore, various kinds of labeled phalloidins (synthesized phalloidin derivatives) are now on the market as specific dyeing agent for actin (e.g. Takara bio Inc. or Invitrogen). Accordingly, in a case where actin is used in asbestos detection, labeled phalloidin can be used suitably in the step of detecting actin binding to asbestos.

The sample is prepared by the following method. However, this is not the only possibility.

An air suspected of containing asbestos dust is filtered through a filter, or a biological sample, such as coughed-up sputum, suspected of containing asbestos is filtered through a filter, and the dust and others collected on the filter are dissolved (suspended) in a suitable buffer solution. Alternatively, the biological sample such as coughed-up sputum can be burned to remove organic substances from it and then dissolved (suspended) in a buffer solution. Furthermore, a building material or the like suspected of containing asbestos may be used as the sample as it is.

To the thus prepared sample is added a solution of the fusion protein of the asbestos binding protein and alkaline phosphatase. Then, asbestos to which the fusion protein has bound is collected from the resulting solution by centrifugation or other method. To the collected asbestos is added chromogenic substrate (BCIP (5-bromo-4-chloro-3-indolyl-phosphate) and NBT (nitro blue tetrazolium)). Thus, it is possible to detect asbestos by measuring the extent to which the asbestos is colored by visual observation or optical absorbance measurement.

Alternatively, by adding the chromogenic substrate directly on the filter after the filtration, it is possible to visually observe the presence or absence of coloring on the filter.

In a case where actin is used, actin is added to the sample prepared as above, asbestos to which actin has bounds is collected by centrifugation or other method, and labeled phalloidin (e.g. fluorescently labeled phalloidin) is added to the collected asbestos. In this manner, it is possible to detect asbestos by observation through a fluorescence microscope or by measurement through a fluorometer.

Standards for certifying a disease caused by asbestos (Labour Standards Bureau of Ministry of Health, Labour and Welfare) are the presence of symptoms of (i) "pleural plaque", which is a pleural thickening, and (ii) "fibrosis", which is hardened lung tissue, identified by chest X-ray or CT (computerized topography). According to these standards, it is certified that a patient has inhaled asbestos the amount of which has twice higher risk of developing lung cancer. However, a patient may develop lung cancer without these symptoms, only by inhalation of asbestos. In view of this, a disease caused by asbestos is also certified according to another standard, i.e. whether or not the number of "asbestos bodies", which are asbestos fibers on which proteins or the like are deposited, is 5000 per gram in lung. Actins binds to asbestos fibers. Therefore, the use of fluorescently labeled phalloidin enables fluorescence observation of asbestos bodies in a tissue section and thus allows for easy determination of the disease caused by asbestos. In this manner, the asbestos binding protein can be used in diagnosis for asbestos-related disorders.

[Asbestos Detection Agent and Asbestos Detection Kit According to the Present Invention]

An asbestos detection agent according to the present invention is an agent containing a protein (asbestos binding protein) capable of binding to asbestos in a solution containing at least 0.1 M or more sodium chloride or an agent containing a fusion protein of (i) a protein (asbestos binding protein) capable of binding to asbestos in a solution containing at least 0.1 M or more sodium chloride and (ii) a reporter protein.

The reporter protein is preferably alkaline phosphatase capable of binding to asbestos.

Constituents other than the asbestos binding protein or the fusion protein are not particularly limited. Note that the protein (asbestos binding protein) capable of binding to asbestos in a solution containing at least 0.1 M or more sodium chloride and the fusion protein are as explained previously. An asbestos detection agent according to the present invention can be used according to the foregoing asbestos detection method.

A detection agent according to the present invention and a detection agent according to the present invention can be used, for example, in the form of asbestos-binding-protein solution, fusion-protein solution, freeze-dried asbestos binding protein, or freeze-dried fusion protein.

Asbestos detection kit according to the present invention includes the asbestos detection agent according to the present invention. Other specific components of the kit are not particularly limited, and the kit may include necessary reagents, equipment, and others selected appropriately. For example, the kit can include a buffer solution for washing, a substrate solution, a tube for reaction, and a filter. Note that the asbestos detection kit according to the present invention can be a kit including an expression vector for the fusion protein of the asbestos binding protein and the reporter protein.

Examples of a specific kit includes a kit consisting of bottle A (buffer solution for washing), bottle B (freeze-dried fusion protein), bottle C (chromogenic substrate solution), a filter, a dropper, an instruction manual, and a color sample.

The term "kit" herein refers to a package including a container (e.g. bottle, plate, tube, dish) for a particular material. The kit is preferably provided with an instruction manual for the use of the material. The instruction manual may be descriptions written or printed on paper or other medium, or may be contained in an electronic medium such as magnetic tape, computer-readable disk or tape, or CD-ROM.

[Screening Method]

A screening method according to the present invention is a method for screening a candidate for an agent aiming at preventing or treating a disease for which asbestos is a causative or worsening factor, the method including: the step of bringing a test substance, asbestos, and actin into contact with each other in a solution containing at least 0.1 M or more sodium chloride; and the step of measuring binding level of the asbestos and the actin in the solution. Note that the screening method of the present invention may include step(s) other than the above steps, and details of the other step(s) are not limited.

With the use of the screening method according to the present invention, it is possible to easily and effectively screen a candidate for an agent aiming at preventing or treating a disease for which asbestos is a causative or worsening factor.

Examples of the disease for which asbestos is a causative or worsening factor include, but not limited to, lung asbestosis, pulmonary asbestosis (pneumonoconiosis), lung cancer, and malignant mesothelioma.

The asbestos binding proteins found from mouse lung-derived proteins by the inventors of the present invention are specifically a mouse cytoplasm-derived γ-actin with an amino acid sequence represented by SEQ ID NO: 21 and a mouse cytoplasm-derived β-actin with an amino acid sequence represented by SEQ ID NO: 23.

However, as described previously, it is known that the structure of actin is conserved with highly excellent conditions in all organisms. Therefore, it can be easily supposed that an actin usable in the screening method of the present invention is not limited to an actin with an amino acid sequence represented by SEQ ID NO: 21 or 23, and all of the actins capable of binding to asbestos can be used in the screening method of the present invention. Particularly, actins of mammals including human, whose amino acid sequence is identical with or highly homologous to the above amino acid sequence represented by SEQ ID NO: 21 or 23, can be used suitably for the screening method of the present invention.

As is known conventionally, actin is a main member constructing cytoskeleton as well as a microtubule and is deeply involved in cell migration such as tumor metastasis. For example, Muller et al. revealed that polymerization and pseudopodia formation of fibrous actin (F-actin) were initiated as a result of interaction between chemokine and receptors CXCR4 and CCR7, in the process of studying the function of chemokine in the migration of tumor cells. That is, it was reported that pseudopodia formation of F-actin, which is one of the main constituents for cytoskeleton, is an important element in the mechanism of cancer cell migration caused by chemokine (Muller A, Homey B, Soto H, Ge N, Catron D, Buchanan M E, McClanahan T, Murphy E, Yuan W, Wagner S N, Barrera J L, Mohar A, Verastegui E, Zlotnik A. Involvement of chemokine receptors in breast cancer metastasis. Nature. 2001 Mar. 1; 410 (6824):50-6.).

As described above, actin is a protein involving in cell migration and essential for living, and is also an important element in the mechanism of tumor metastasis. Therefore, it can be sufficiently expected that binding of actin to asbestos due to inhalation of asbestos powder dust causes some kind of change in the function of actin and result in health problems. Consequently, it can be easily understood that a substance capable of inhibiting binding of actin to asbestos can be a candidate for an agent aiming at preventing or treating a disease for which asbestos is a causative or worsening factor.

The step of bringing a test substance, asbestos, and actin into contact with each other in a solution containing at least 0.1 M or more sodium chloride is realized, for example, by addition of a test substance, asbestos, and actin to a solution containing 0.1M sodium chloride. However, results can vary depending upon the order of the test substance, asbestos, and actin to be added. In view of this, it is preferable to prepare independent subject groups for each order of addition. Further, it is preferable to provide a control group in which the test substance is not added. A concentration of sodium chloride contained in the solution is not limited as long as it is higher than at least 0.1 M, and may be set to be a suitable concentration according to specific asbestos and asbestos binding protein. Note that the "solution containing at least 0.1 M or more sodium chloride" is a solution excluding a sodium chloride concentration of below 0.1 M.

A mixture solution of the test substance, asbestos, and actin is preferably incubated at a temperature in the range from 4° C. to room temperature for approximately 5 to 30 minutes, for example. However, the incubation conditions are not limited to this.

In the step of measuring binding level of the asbestos and the actin in the solution, binding level of asbestos and actin in the mixture solution of the test substance, asbestos, and actin is measured. Specifically, actin not binding to asbestos is removed from the mixture solution, for example, by centrifugation, filtration, or other method, and actin binding to asbestos is then detected. By comparison between the result of the subject groups and the result of the control group, it is possible to determine the binding inhibition strength of the test substrate.

For the detection of actin binding to asbestos, the foregoing labeled phalloidin can be used suitably.

The candidate for an agent aiming at preventing or treating a disease for which asbestos is a causative or worsening factor is preferably a substance which inhibits binding of asbestos and actin in the control group in which the test substance is not added to decrease their binding level by 50%, more preferably 70%, further preferably 90%, particularly preferably 100%.

A substance obtained by the screening method of the present invention is useful as the candidate for an agent aiming at preventing or treating a disease for which asbestos is a causative or worsening factor. Furthermore, if effectiveness of the obtained candidate is found by a pharmacological test, the candidate becomes an effective component of an agent aiming at preventing or treating a disease for which asbestos is a causative or worsening factor.

In addition, the substance obtained by the screening method of the present invention is very useful as a research tool for the mechanism of asbestos working as a causative or worsening factor for a disease.

EXAMPLE 1

Asbestos (Chrysotile) Binding Protein (1) Bacterial Strains as Used

The following three types of bacterial strains were used: *Escherichia coli* K12 (ATCC 700926); *Pseudomonas putida* KT2440; and *Corynebacterium glutamicum* ATCC 13032.

(2) Preparation of Cell Lysate

Each type of the bacterial strains was cultured overnight at 37° C. in 2×YT medium. Then, 1% of the obtained bacteria was inoculated into another 2×YT medium and cultured therein at 37° C. for 4 hours. The cultured bacteria were centrifuged to be collected, and then the collected bacteria was suspended in 50 mM Tris-HCl having pH 7.5 with sucrose concentration of 10%. The suspension was subjected to freeze thawing, and lysozyme was added thereto at a concentration of 250 μg/ml. The resulting solution was left on ice for 30 minutes. After reacted at 37° C. for 5 minutes, the solution was left on ice for another 10 minutes, and subjected to ultrasonic disruption until its viscosity was lost. Then, each solution was centrifuged for 15 minutes at 20,000×g, and the obtained supernatant was used as a cell lysate.

(3) Obtaining of Asbestos (Chrysotile) Binding Protein

The obtained cell lysate was diluted with 25 mM Tris-HCl having pH 7.5, 0.5% Tween20, 0.1M NaCl so as to prepare a solution with a protein concentration of 1 mg/ml. To 1 ml of the prepared solution was added 5 mg of chrysotile (white asbestos, Japan Association for Working Environment Measurement). The resulting solution was mixed by inversion at 4° C. for 30 minutes. After centrifugation (10,000×g, 3 minutes), the supernatant was removed. To the precipitate were added 1 ml of solution containing 25 mM Tris-HCl having pH 7.5, 0.5% Tween20, and 0.1M NaCl, and the resulting solution was vortexed to dissolve. Such a washing operation was performed three times in total. To the precipitate obtained after the washing, 50 μl of SDS sample buffer (1% dodecyl sodium sulfate [SDS], 75 mM Tris-HCl pH 7.5, 10% glycerol, 1% beta-mercaptoethanol) was added, and the resulting solution was incubated at 100° C. for 5 minutes. The extracted protein was separated by a typical polyacrylamide electrophoresis (Laemmli method).

FIG. 1 shows the result of electrophoresis with the use of *Escherichia coli* K12. As is apparent from FIG. 1, bands of asbestos (chrysotile) binding protein (hereinafter referred to as "asbestos binding protein") were found at the positions corresponding to molecular weights of approximately 14 kD, 15 kD, 17 kD, 20 kD, 37 kD, 40 kD, and 65 kD.

Figure 2:
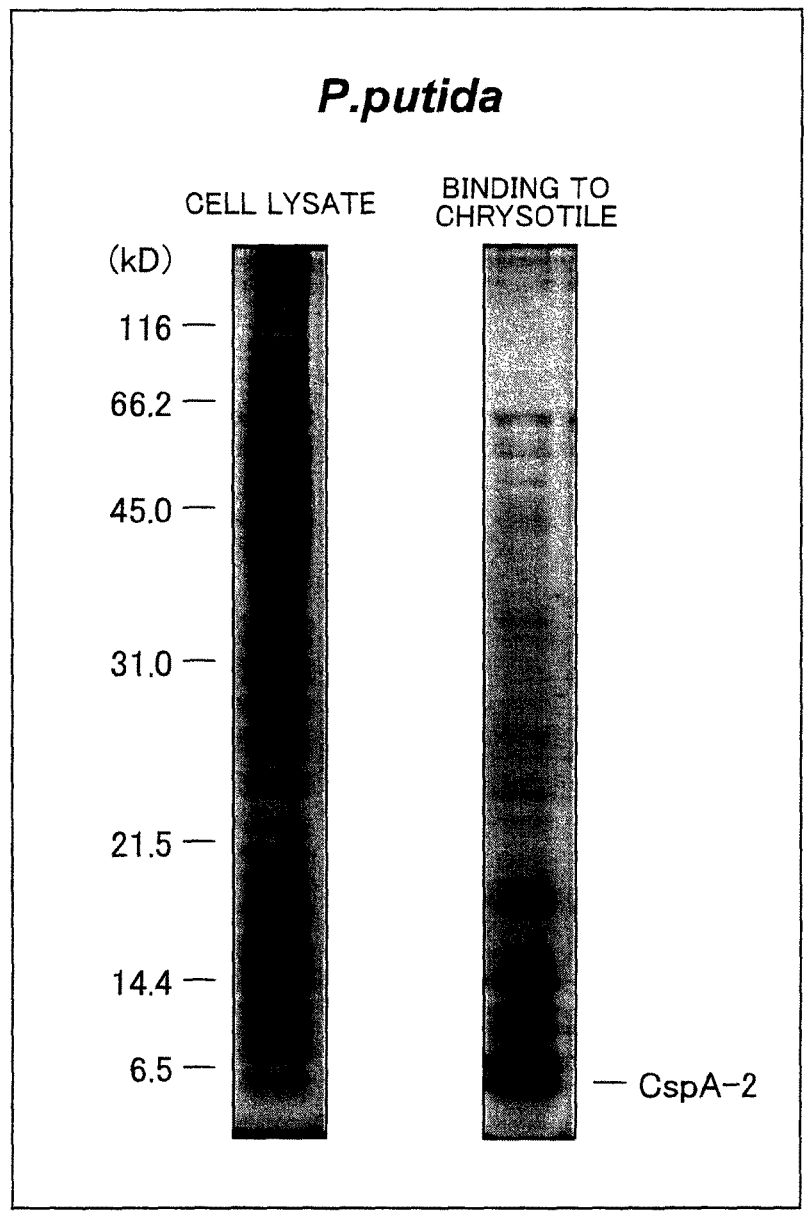
FIG. 2 is an electrophoretogram showing that an asbestos (chrysotile) binding protein was obtained from a cell lysate of *Pseudomonas putida* KT2440.

FIG. 2 shows the result of electrophoresis with the use of *Pseudomonas putida* KT2440. As is apparent from FIG. 2, a band of the asbestos binding protein was found at the position corresponding to molecular weight of approximately 5 kD.

Figure 3:
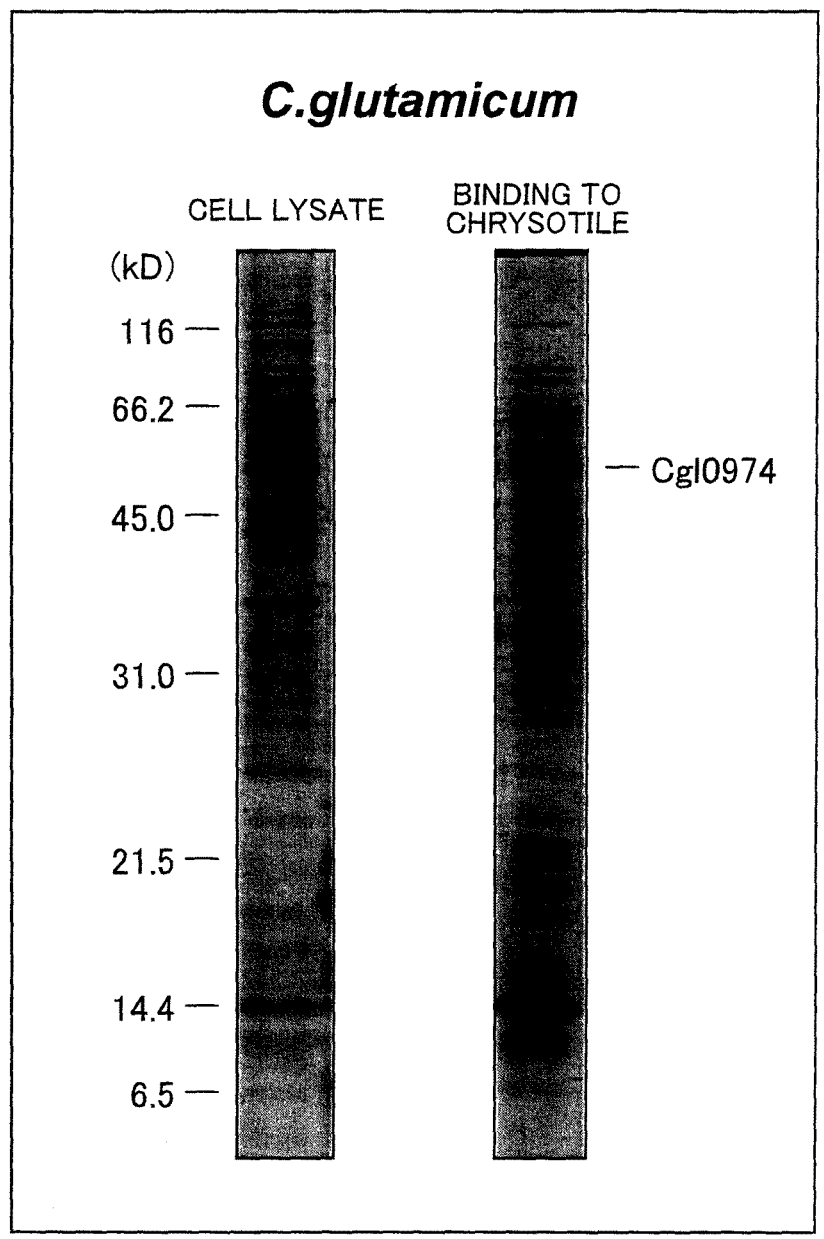
FIG. 3 is an electrophoretogram showing that an asbestos (chrysotile) binding protein was obtained from a cell lysate of *Corynebacterium glutamicum* ATCC13032.

FIG. 3 shows the result of electrophoresis with the use of *Corynebacterium glutamicum* ATCC13032. As is apparent from FIG. 3, a band of the asbestos binding protein was found at the position corresponding to molecular weight of approximately 50 kD.

(4) Determination of Amino Acid Sequence and Base Sequence

The obtained protein was separated by polyacrylamide gel electrophoresis, and transferred on a polyvinylidene difluoride (PVDF) film. The film was stained with coomassie brilliant blue, and thereafter a band of the target protein was cut out. A portion of the film was immersed into 100% acetonitrile, and then reacted at 37° C. for 30 minutes in 100 μl of solution containing 100 mM acetic acid, 0.5% polyvinylpyrrolidone K-30, and 1% methionine. After washed with 1 ml of ultrapure water 10 times, the film portion was further washed with 100 μl of solution containing 50 mM ammonium bicarbonate and 5% acetonitrile 3 times. Then, the film portion was digested at 37° C. for 24 hours in 20 μl of 0.5 μg/ml trypsin solution (50 mM ammonium bicarbonate, 5% acetonitrile). A tryptic digest was desalted with ZipTipC18 (Millipore). Desalting was performed by a method according to Millipore's protocol. The desalted sample was analyzed by matrix-assisted laser desorption/ionization time-of-flight mass spectrometer (BiflexIV: BRUKER DALTONICS), and the protein and a gene encoding the protein was identified by peptide mass fingerprint analysis. An amino acid sequence of the identified protein was obtained from database (DDBJ). A base sequence of the gene encoding the identified protein was also obtained from database (DDBJ).

As a result of this, it was found out that *Escherichia coli* K12-derived asbestos binding protein at an approximately 65 kD molecular weight band was a protein with an amino acid sequence represented by SEQ ID NO: 1 (ACCESSION:NP_414555), and the protein was encoded by a gene (dnaK) with a base sequence represented by SEQ ID NO: 2.

It was found out that *Escherichia coli* K12-derived asbestos binding protein at an approximately 37 kD molecular weight band was a protein with an amino acid sequence represented by SEQ ID NO: 3 (ACCESSION:NP_415477), and the protein was encoded by a gene (ompA) with a base sequence represented by SEQ ID NO: 4.

It was found out that *Escherichia coli* K12-derived asbestos binding protein at an approximately 40 kD molecular weight band was a protein with an amino acid sequence represented by SEQ ID NO: 5 (ACCESSION:NP_416719), and the protein was encoded by a gene (ompC) with a base sequence represented by SEQ ID NO: 6.

It was found out that *Escherichia coli* K12-derived asbestos binding protein at an approximately 17 kD molecular weight band was a protein with an amino acid sequence represented by SEQ ID NO: 7 (ACCESSION:NP_414720), and the protein was encoded by a gene (hlpA) with a base sequence represented by SEQ ID NO: 8.

It was found out that *Escherichia coli* K12-derived asbestos binding protein at an approximately 14 kD molecular weight band was a protein with an amino acid sequence represented by SEQ ID NO: 9 (ACCESSION:NP_417496), and the protein was encoded by a gene (ygiW) with a base sequence represented by SEQ ID NO: 10.

It was found out that *Escherichia coli* K12-derived asbestos binding protein at an approximately 20 kD molecular weight band was a protein with an amino acid sequence represented by SEQ ID NO: 11 (ACCESSION:NP_414687), and the protein was encoded by a gene (dksA) with a base sequence represented by SEQ ID NO: 12.

It was found out that *Escherichia coli* K12-derived asbestos binding protein at an approximately 15 kD molecular weight band was a protein with an amino acid sequence represented by SEQ ID NO: 13 (ACCESSION:NP_415753), and the protein was encoded by a gene (hns) with a base sequence represented by SEQ ID NO: 14.

It was found out that *Pseudomonas putida* KT2440-derived asbestos binding protein at an approximately 5 kD molecular weight band was a protein with an amino acid sequence represented by SEQ ID NO: 15 (ACCESSION: NP_744611), and the protein was encoded by a gene (cspA-2) with a base sequence represented by SEQ ID NO: 16.

It was found out that *Corynebacterium glutamicum* ATCC13032-derived asbestos binding protein at an approximately 50 kD molecular weight band was a protein with an amino acid sequence represented by SEQ ID NO: 17 (ACCESSION:NP_600201), and the protein was encoded by a gene (Cgl0974) with a base sequence represented by SEQ ID NO: 18.

The following experiment was conducted using the *Escherichia coli* K12-derived asbestos binding protein (DksA) at an approximately 20 kD molecular weight band and the *Escherichia coli* K12-derived asbestos binding protein (PhoA: alkaline phosphatase (ACCESSION: NP_414917), hereinafter referred to as "AP") at an approximately 50 kD molecular weight band. An amino acid sequence of the AP was represented by SEQ ID NO: 19, and a base sequence of a gene encoding the AP was represented by SEQ ID NO: 20.

(5) Construction of Expression Vector of DksA-AP Fusion Protein

First, AP expression vector was constructed. Two types of oligonucleotide primers, P1: GTTAAGCTTCGGACACCA-GAAATGCCTGT (SEQ ID NO: 31) and P2: GTTGCGGC-CGCTTTCAGCCCCAGAGCGGCT (SEQ ID NO: 32), were produced based on a known phoA gene sequence (SEQ ID NO: 20). PCR was performed with the oligonucleotide primers P1 and P2 by using a chromosome of *Escherichia coli* K12 as a template. The reaction was performed using KOD Plus DNA polymerase (TOYOBO) according to TOYOBO's protocol. PCR products and expression vector pET21-b (Novagen) were treated with restriction enzymes HindIII and NotI at 37° C. for 2 hours, and then subjected to agarose gel electrophoresis. Each of the respective DNA fragments cut out from gel was ligated with Ligation High (TOYOBO) at 16° C. for 2 hours, and then transformed into *Escherichia coli*

MV1184. From the obtained colony, a plasmid into which the target DNA fragment was inserted was extracted. The plasmid was named as pET AP.

Next, DksA-AP expression vector was constructed. Two types of oligonucleotide primers, P3: GGAATTCGCTAG-CATGCAAGAAGGGCAAAACCG (SEQ ID NO: 33) and P4: GTTGGATCCCCGCCAGCCATCTGTTTTCGC (SEQ ID NO: 34), were produced based on a base sequence (SEQ ID NO: 12). PCR was performed with the oligonucleotide primers P3 and P4 by using a chromosome of *Echerichia coli* K12 as a template. PCR products and the pET AP were treated with restriction enzymes NheI and BamHI at 37° C. for 2 hours, and then subjected to agarose gel electrophoresis. Each of the respective DNA fragments cut out from gel was ligated with Ligation High (TOYOBO) at 16° C. for 2 hours, and then transformed into *Echerichia coli* MV1184. From the obtained colony, a plasmid into which the target DNA fragment was inserted was extracted. The plasmid was named as pET DksA-AP.

(6) Expression of AP Protein and DksA-AP Fusion Protein

Rosetta BL21 (DE3) pLysS (Novagen) which had been transformed with the pET AP or the pET DksA-AP was cultured overnight at 37° C. in 2×YT medium. Then, 1% of the obtained cells was inoculated into another 2×YT medium. After the cells were cultured at 28° C. until OD600 reached 0.6, IPTG was added to the cultured cells so that a final concentration became 0.2 mM. Then, the resulting solution was cultured for 4 hours. The pellet was suspended with 500 μl of buffer solution (25 mM Tris-HCl having pH 7.5, 0.5% Tween20), and the suspension was subjected to ultrasonic disruption. Thereafter, the obtained solution was centrifuged for 15 minutes at 20,000×g to obtain respective supernatants. The obtained supernatants were a cell lysate containing AP protein (hereafter referred to as "AP cell lysate") and a cell lysate containing DksA-AP fusion protein (hereafter referred to as "DksA-AP cell lysate"), respectively.

(7) Confirmation of Binding of AP Protein and DksA-AP Fusion Protein to Asbestos (Chrysotile)

50 μl of AP cell lysate or DksA-AP cell lysate was mixed with 950 μl of buffer solution (25 mM Tris-HCl having pH 7.5, 0.5% Tween20). Thereafter, 5 mg of asbestos (chrysotile, Japan Association for Working Environment Measurement) was added to each mixture solution, and the resulting solution was left at room temperature for 5 minutes for binding. The asbestos was precipitated by centrifugation (10,000×g, 3 minutes), and suspended with a buffer solution (25 mM Tris-HCl having pH 7.5, 0.5% Tween20) having NaCl concentration of 0 mM, 100 mM, or 300 mM. Then, the asbestos was collected by another centrifugation, and proteins binding to the asbestos were determined by electrophoresis.

Figure 4A:
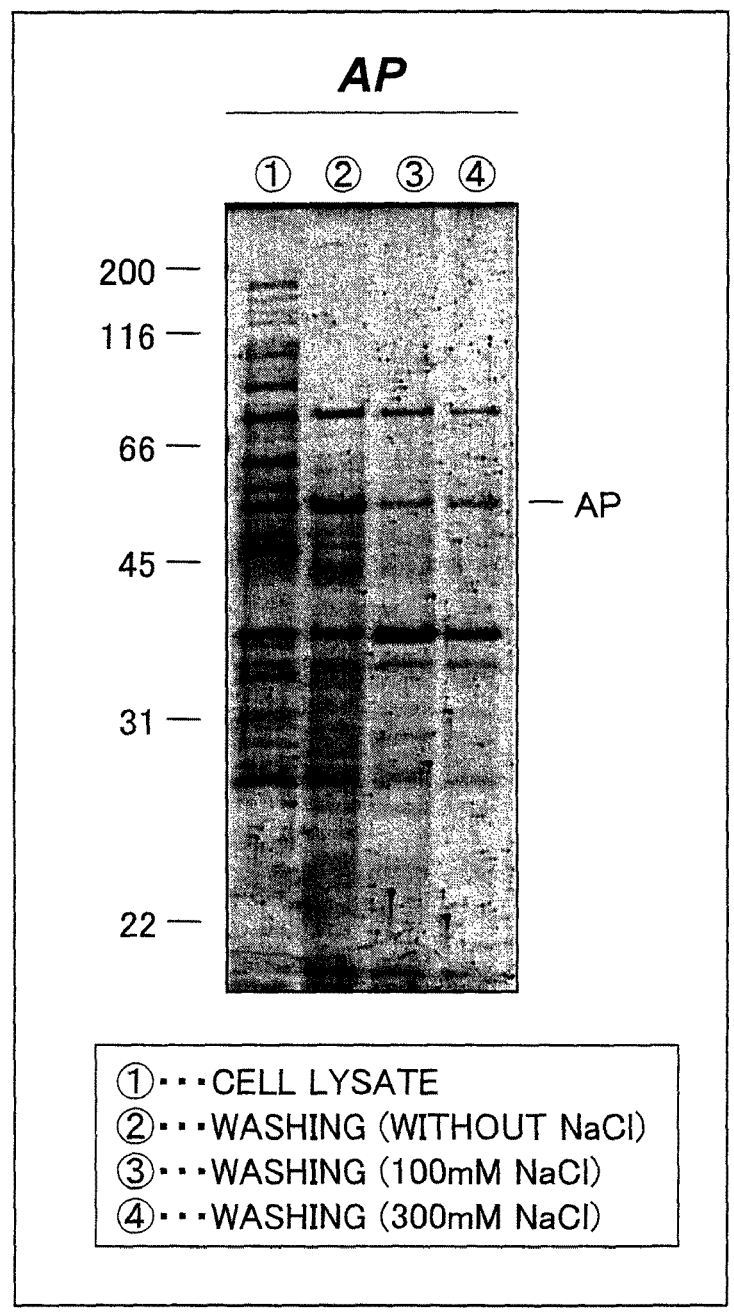
FIG. 4(*a*) is an electrophoretogram showing that AP protein binds to asbestos (chrysotile).
Figure 4B:
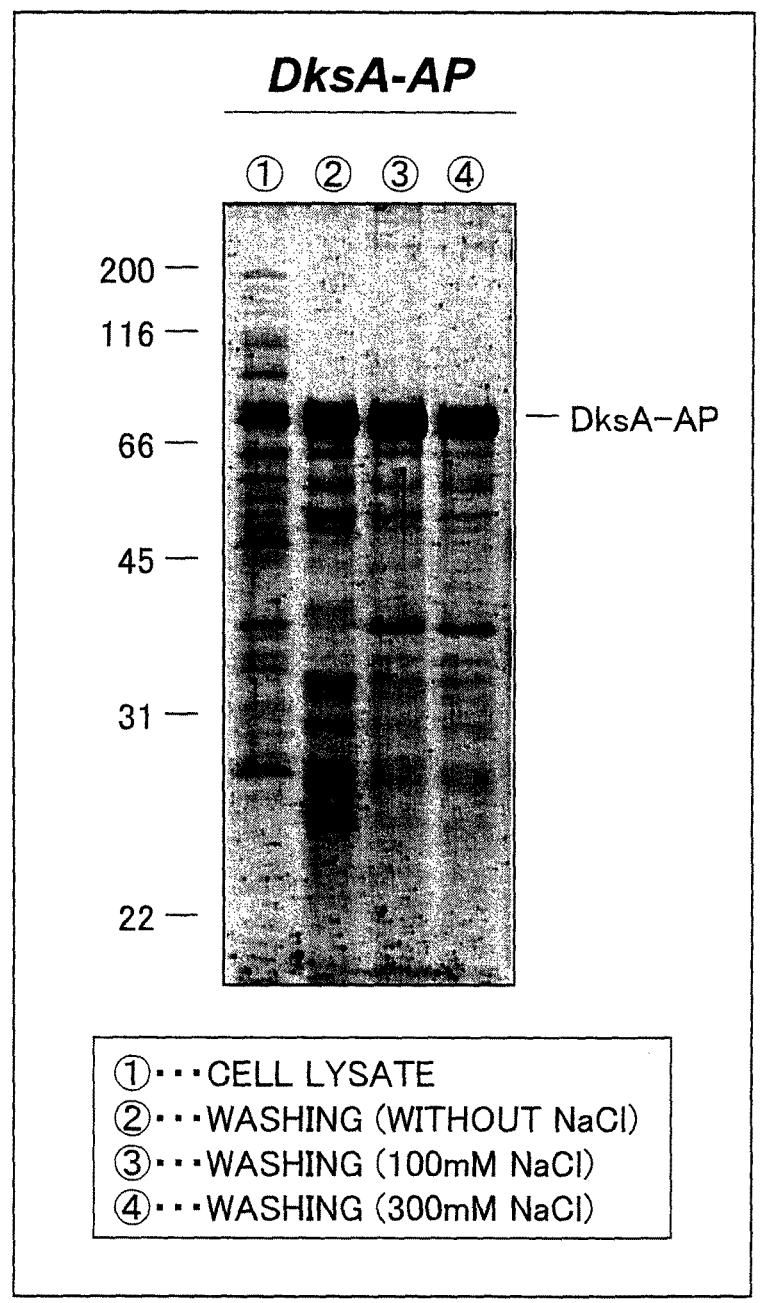

FIGS. 4(*a*) and 4(*b*) show the results of electrophoresis. FIG. 4(*a*) shows the result of electrophoresis using the AP cell lysate. FIG. 4(*b*) shows the result of electrophoresis using the DksA-AP cell lysate. In both FIGS. 4(*a*) and 4(*b*), lane 1 shows the result of electrophoresis with the use of only 0.2 μl of cell lysate as a sample, lane 2 shows the result of electrophoresis in which proteins binding to asbestos precipitate which proteins were obtained by using the buffer solution without containing NaCl were used as a sample, lane 3 shows the result of electrophoresis in which proteins binding to asbestos precipitate which proteins were obtained by using the buffer solution containing 100 mM NaCl were used as a sample, and lane 4 shows the result of electrophoresis in which proteins binding to asbestos precipitate which proteins were obtained by using the buffer solution containing 300 mM NaCl were used as a sample.

As is apparent from FIG. 4(*a*), it was confirmed that the AP had the capability of weakly binding to asbestos. As is apparent from FIG. 4(*b*), the DksA-AP fusion protein tightly bound to asbestos and was in the concentrated state in the asbestos precipitate.

(8) Detection of Binding of DksA-AP Fusion Protein to Asbestos (Chrysotile) by Coloring 50 μl of AP cell lysate, 50 μl of DksA-AP cell lysate, or *Echerichia coli*-derived cell lysate in which recombinant protein was not made expressed was mixed with 950 μl of buffer solution (25 mM Tris-HCl having pH 7.5, 0.5% Tween20). Thereafter, 5 mg of asbestos (chrysotile) was added to each mixture solution, and the resulting solution was left at room temperature for 5 minutes for binding. In addition, two controls were prepared. One of the controls was obtained without addition of asbestos, and the other was obtained without using any cell lysates. The asbestos was precipitated by centrifugation (10,000×g, 3 minutes), and suspended with a buffer solution (25 mM Tris-HCl having pH 7.5, 0.5% Tween20) without containing NaCl. Then, the asbestos was collected by another centrifugation.

The collected asbestos was suspended with 100 μl of coloring reagent (100 mM Tris-HCl having pH 9.5, 100 mM NaCl, 50 mM MgCl2, 0.4 mM BCIP, 0.3 mM NBT), and the suspension was reacted at 37° C. for 5 minutes. The samples after the reaction were moved on a 96-well plate and scanned by a scanner. Note that BCIP (5-bromo-4-chloro-3-indolyl-phosphate) and NBT (nitro blue tetrazolium) are generally used as chromogenic substrates of alkaline phosphatase.

Figure 5:
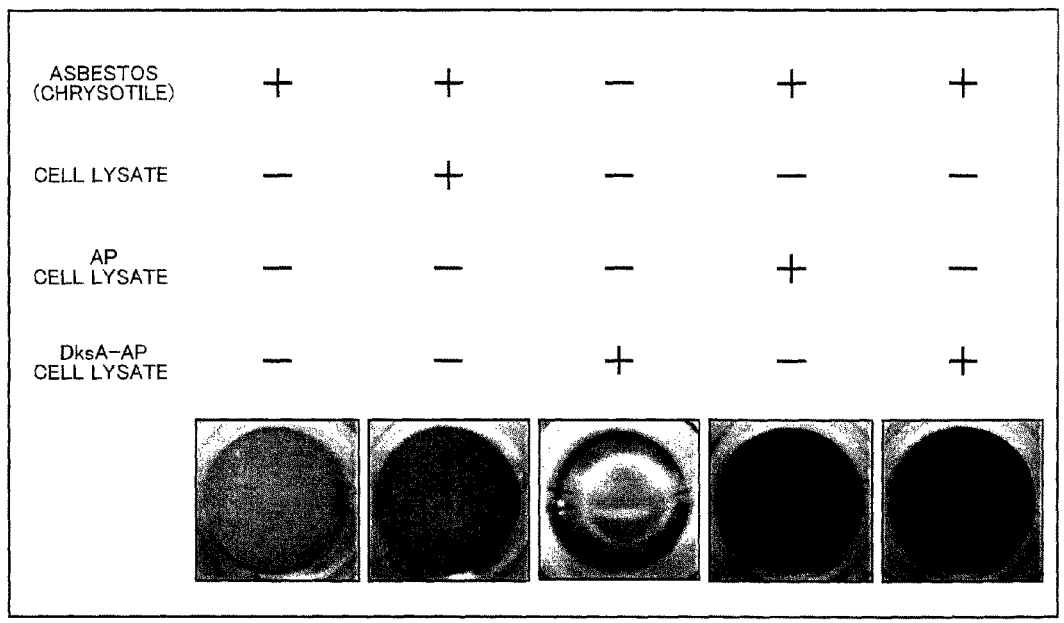
FIG. 5 is a view showing that asbestos (chrysotile) was detected by coloring with the use of DksA-AP fusion protein.

FIG. 5 shows the results. As is apparent from FIG. 5, the followings were confirmed. That is, in a case where the *Echerichia coli*-derived cell lysate in which DksA-AP fusion protein or AP was not made expressed was used, no coloring was recognized even under circumstances where no asbestos existed. However, in cases where the AP cell lysate and the DksA-AP cell lysate were used, coloring was recognized under circumstances where asbestos existed. As a result of comparison between the case where the AP cell lysate was used and the case where the DksA-AP cell lysate was used, it became evident that a higher level of asbestos-binding activity was obtained by using the DksA-AP cell lysate.

(9) Consideration of Sensitivity Measured by an Asbestos (Chrysotile) Detecting System Using DksA-AP Fusion Protein 10 μl of DksA-AP cell lysate was mixed with 90 μl of buffer solution (25 mM Tris-HCl having pH 7.5, 0.5% Tween20). Thereafter, 0 mg, 0.005 mg, 0.01 mg, 0.05 mg, 0.1 mg, 0.5 mg, or 1 mg of asbestos (chrysotile, Japan Association for Working Environment Measurement) was added to the mixture solution, and the mixture solution was left at room temperature for 5 minutes for binding. The asbestos was precipitated by centrifugation (10,000×g, 3 minutes), and suspended with a buffer solution (25 mM Tris-HCl having pH 7.5, 0.5% Tween20) without containing NaCl. Then, the asbestos was collected by another centrifugation.

The collected asbestos was suspended with 100 μl of coloring reagent (100 mM Tris-HCl having pH 9.5, 100 mM NaCl, 50 mM MgCl2, 0.4 mM BCIP, 0.3 mM NBT), and the suspension was reacted at 37° C. for 5 to 60 minutes. The samples after the reaction were moved on a 96-well plate, and optical absorbance was measured by using a plate reader.

Figure 6:
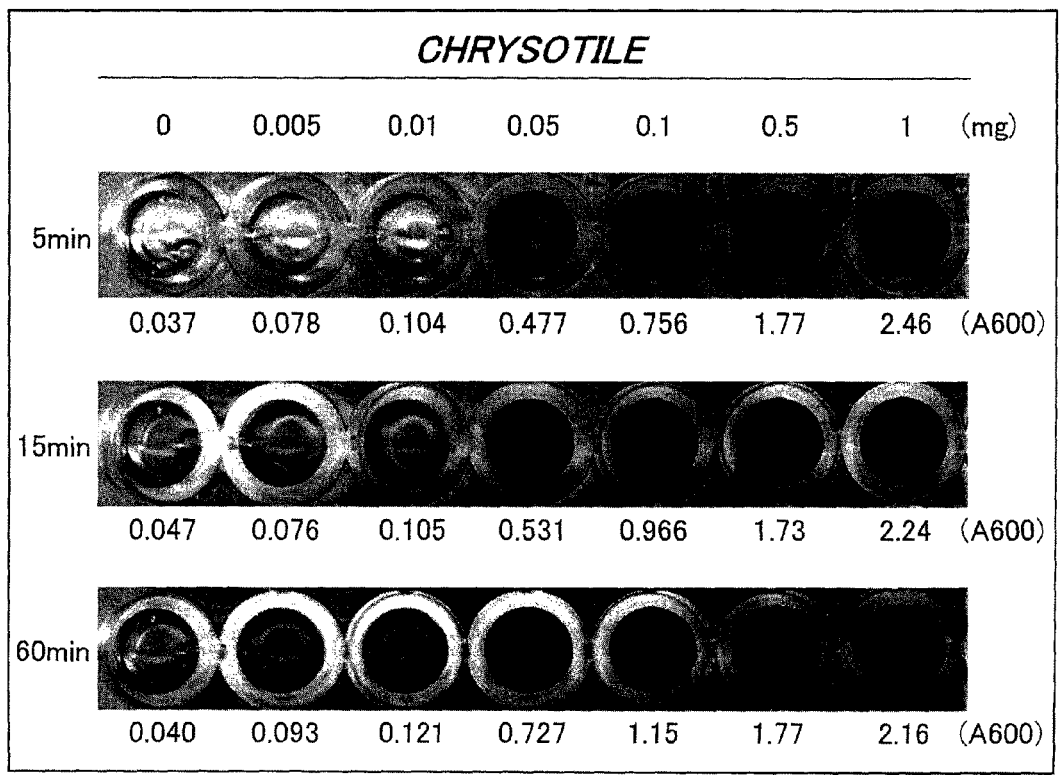
FIG. 6 is a view showing the result of measurement of detection sensitivities in a system of detecting asbestos (chrysotile) by coloring with the use of DksA-AP fusion protein.

FIG. 6 shows the results. In this experiment system, it was found that asbestos detection sensitivity by visual observation was approximately 50 μg, and detection sensitivity by plate reader was approximately 5 μg. A longer coloring reaction time slightly improved detection sensitivity and allows 10 μg of asbestos to be detected by visual observation.

(10) Asbestos (Chrysotile) Detection Using Filter

10 μl of DksA-AP cell lysate was mixed with 990 μl of buffer solution (25 mM Tris-HCl having pH 7.5, 0.5% Tween20). Thereafter, 0 μg, 5 μg, and 50 μg of asbestos (chrysotile, Japan Association for Working Environment Measurement) each were added to the mixture solution, and the obtained mixture solutions were left at 4° C. for 15 minutes for binding. After the binding, the solutions were filtered through DURAPORE MEMBRANE FILTERS (13 mm in diameter, 0.45 mm in pore diameter, MILLIPORE) placed on a SWINNEX filter holder (MILLIPORE), by using a 1 ml-syringe. Each of the filters was washed with 1 ml of the above-mentioned buffer solution three times. Thereafter, each of the filters was reacted at 37° C. for 10 minutes with its surface covered with 50 μl of coloring reagent (100 mM Tris-HCl having pH 9.5, 100 mM NaCl, 50 mM MgCl2, 0.4 mM BCIP, 0.3 mM NBT). After the reaction, the filters were dried and scanned by a scanner.

Figure 7:
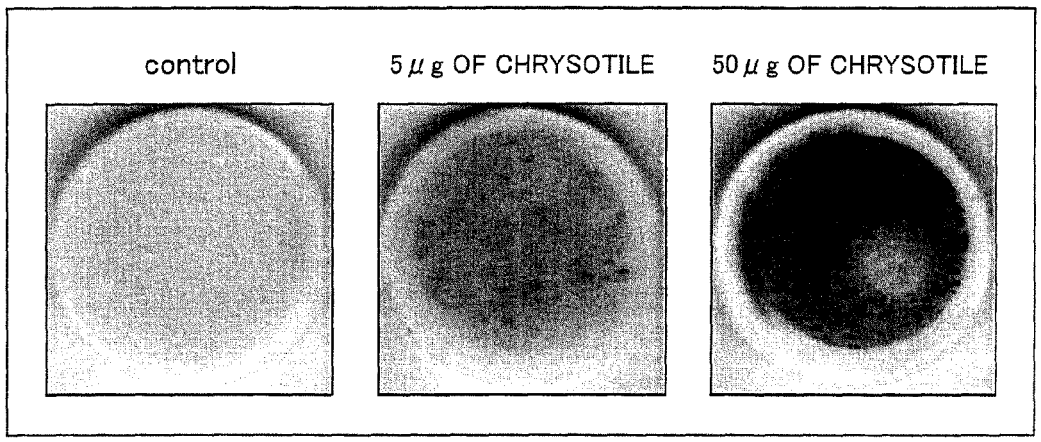
FIG. 7 is a view showing the result of asbestos (chrysotile) detection by using DksA-AP fusion protein and a filter.

FIG. 7 shows the results. As is apparent from FIG. 7, in the case of detection through the filter, 5 μg of asbestos was detected by visual observation. As shown in FIG. 6, detection sensitivity by visual observation with the use of 96-well plate was approximately 50-μg. As a result of comparison, it became evident that a detecting system using filters brings a higher detection sensitivity by visual observation.

EXAMPLE 2

Asbestos (Chrysotile)-Binding Mouse Lung (1) Mouse Lung as Used

Mouse lung was purchased from Funakoshi Corporation (Product code: J110, a line of mouse: C57BL/6J).

(2) Preparation of Sample

To mouse lung (170 mg) were added 1.7 ml of M-PER® (manufactured by PIERCE, mammalian protein extraction reagent) and 0.017 ml of protease inhibitor (manufactured by Sigma Corporation). The mixture solution was subjected to ultrasonic treatment (for 7.5 minutes) to disrupt the cells. Then, the solution was subjected to centrifugation (10,000×g, 15 minutes) to collect the supernatant. Further, the collected supernatant was subjected to centrifugation (10,000×g, 20 minutes) to collect the supernatant as a sample.

(3) Obtaining of Asbestos (Chrysotile)-Binding Mouse Lung Protein

To 0.15 ml of the obtained sample (protein concentration: 4 mg/ml) was added 0.45 ml of buffer solution (25 mM Tris-HCl having pH 8.0, 0.5% Tween20, 0.1M NaCl). A total amount of the obtained solution (protein concentration: 1 mg/ml) was 0.6 ml. To the obtained solution was added 5 mg of chrysotile (white asbestos, Japan Association for Working Environment Measurement). The resulting solution was mixed by inversion at 4° C. for 30 minutes. Thereafter, the solution was subjected to centrifugation (20,000×g, 10 minutes), and asbestos (chrysotile) was collected as a precipitate. To the precipitate was added buffer solutions (25 mM Tris-HCl having pH 8.0, 0.5% Tween20) respectively containing 0.5 M and 1M NaCl 25, and the resulting solution was vortexed to dissolve. Such a washing operation was performed three times in total. To the precipitate obtained after the washing, 50 μl of SDS sample buffer (1% dodecyl sodium sulfate [SDS], 75 mM Tris-HCl having pH 7.5, 10% glycerol, 1% beta-mercaptoethanol) was added, and the resulting solution was incubated at 100° C. for 5 minutes. The extracted protein was separated by a typical polyacrylamide electrophoresis (Laemmli method).

Figure 8:
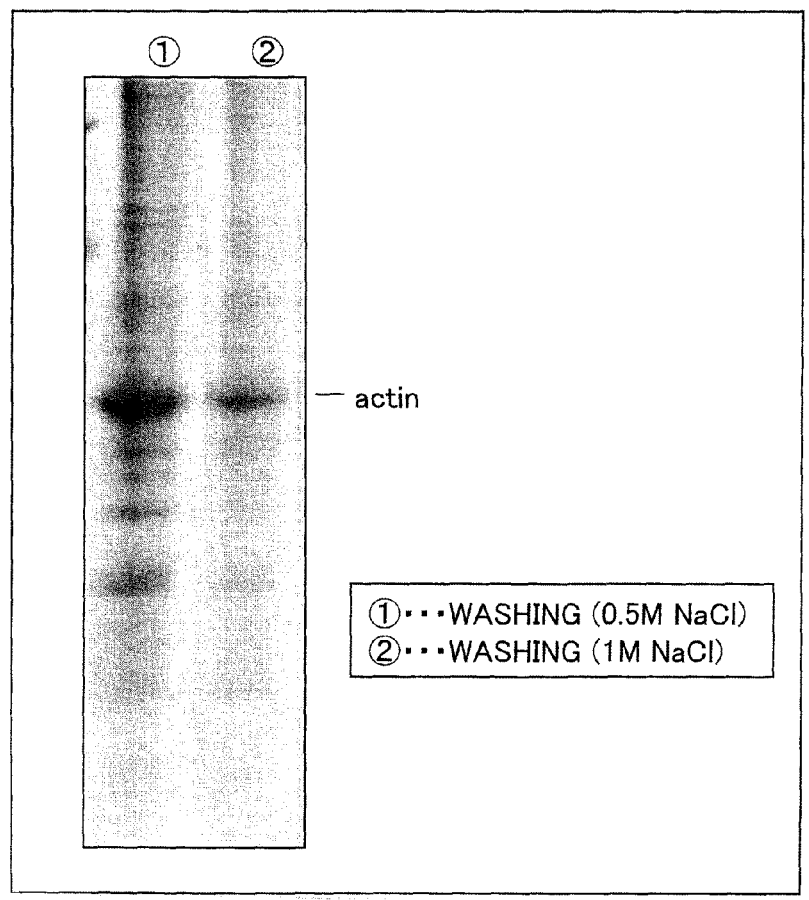
FIG. 8 is an electrophoretogram showing that an asbestos (chrysotile) binding protein was obtained from a mouse lung protein sample.

FIG. 8 shows the results. In FIG. 8, lane 1 shows the result of electrophoresis in which proteins binding to asbestos (chrysotile) which proteins were obtained after washed with the buffer solution containing 0.5 M NaCl were used, and lane 2 shows the result of electrophoresis in which proteins binding to asbestos (chrysotile) which proteins were obtained after washed with the buffer solution containing 1 M NaCl were used. As is apparent from FIG. 8, a band of asbestos binding protein was found at the position corresponding to molecular weight of approximately 42 kD, even at a high salt concentration (1M NaCl).

(4) Determination of Amino Acid Sequence and Base Sequence

An amino acid sequence of the asbestos binding protein and a base sequence of a gene encoding the asbestos binding protein were determined by a method as in Example 1. As a result of this, it was revealed that the asbestos binding protein was at least one type of a protein (ACCESSION: NM_009609) with an amino acid sequence represented by SEQ ID NO: 21 and a protein (ACCESSION: NM_007393) with an amino acid sequence represented by SEQ ID NO: 23. That is, it was revealed that the asbestos binding protein was actin. Note that the protein with an amino acid sequence represented by SEQ ID NO: 21 is a protein encoded by a gene (actg1) with a base sequence represented by SEQ ID NO: 22, and the protein with an amino acid sequence represented by SEQ ID NO: 23 is a protein encoded by a gene (actb) with a base sequence represented by SEQ ID NO: 24.

EXAMPLE 3

Asbestos (Crocidolite and Amosite) Binding Protein (1) Bacterial Strains as Used In Example 3 were used the following two types of bacterial strains: *Escherichia coli* K12 (ATCC 700926); and highly thermophilic bacterium (*Thermus thermophilus*) HB27 (ATCC BAA-163).

(2) Preparation of Cell Lysate

A cell lysate was prepared by a method as in Example 1.

(3) Obtaining of Asbestos (Crocidolite and Amosite) Binding Protein

The obtained cell lysate was diluted with 25 mM Tris-HCl having pH 8.0, 0.5% Tween20, 0.1M NaCl so as to prepare a solution with a protein concentration of 1 mg/ml. To 1 mL of the prepared solution was added 5 mg of amosite (blue asbestos, Japan Association for Working Environment Measurement) and crocidolite (brown asbestos, Japan Association for Working Environment Measurement). The respective resulting solutions were mixed by inversion at 4° C. for 30 minutes. After centrifugation (10,000×g, 3 minutes), the supernatant was removed. To the precipitate were added 1 ml of solution containing 25 mM Tris-HCl having pH 8.0, 0.5% Tween20, and 0.1M NaCl, and the resulting solution was vortexed to dissolve. Such a washing operation was performed three times in total. To the precipitate obtained after the washing, 50 μl of SDS sample buffer (1% dodecyl sodium sulfate [SDS], 75 mM Tris-HCl pH 7.5, 10% glycerol, 1% beta-mercaptoethanol) was added, and the resulting solution was incubated at 100° C. for 5 minutes. The extracted protein was separated by a typical polyacrylamide electrophoresis (Laemmli method).

Figure 9:
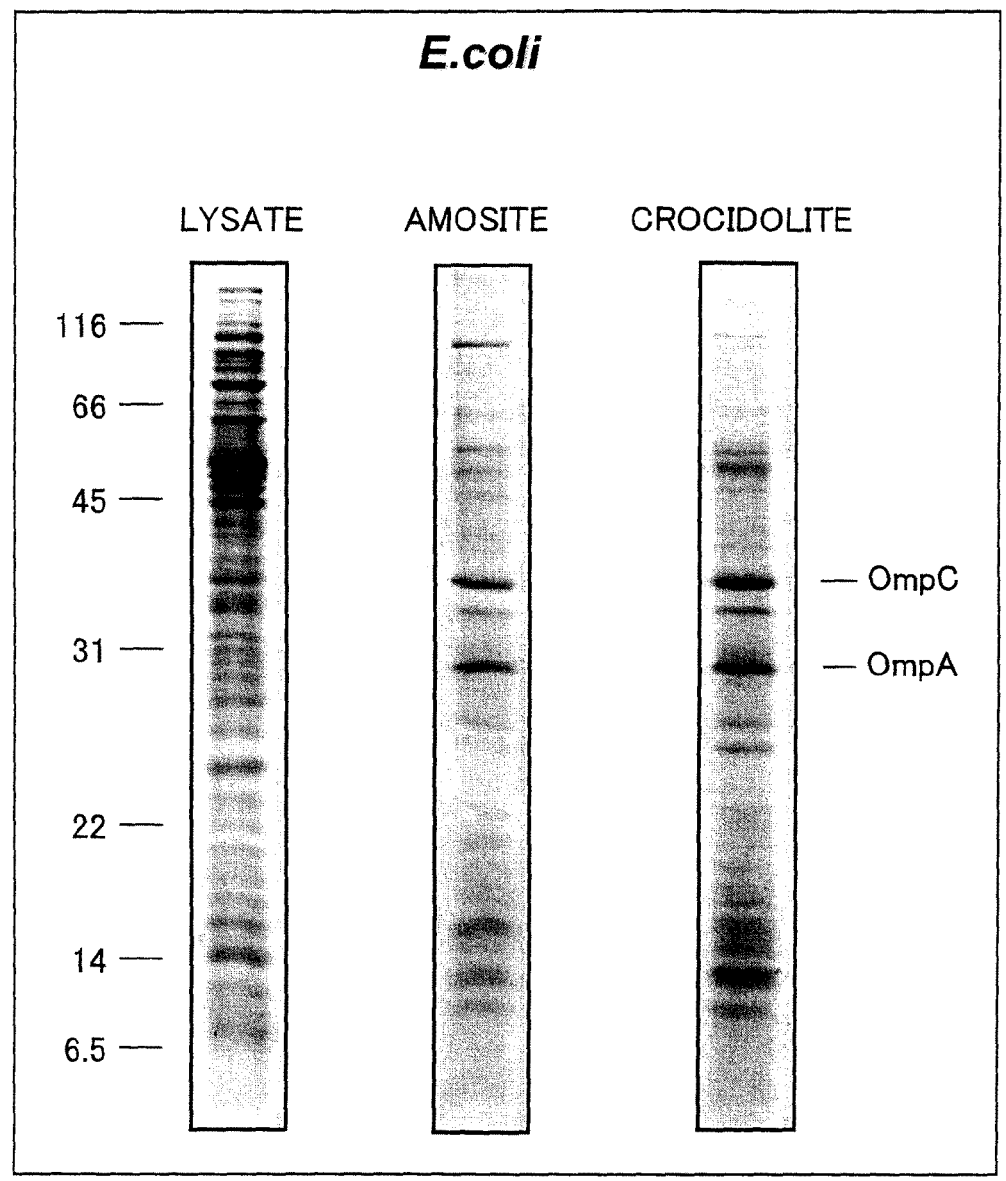
FIG. 9 is an electrophoretogram showing that an asbestos (crocidolite/amosite) binding protein was obtained from a cell lysate of *Escherichia coli* K12.

FIG. 9 shows the result of polyacrylamide electrophoresis using *Escherichia coli* K12. As is apparent from FIG. 9, there was no difference between a band pattern of amosite and a band pattern of crocidolite, and bands of asbestos binding protein were found at the positions corresponding to molecular weights of approximately 30 kD and 40 kD.

Figure 10:
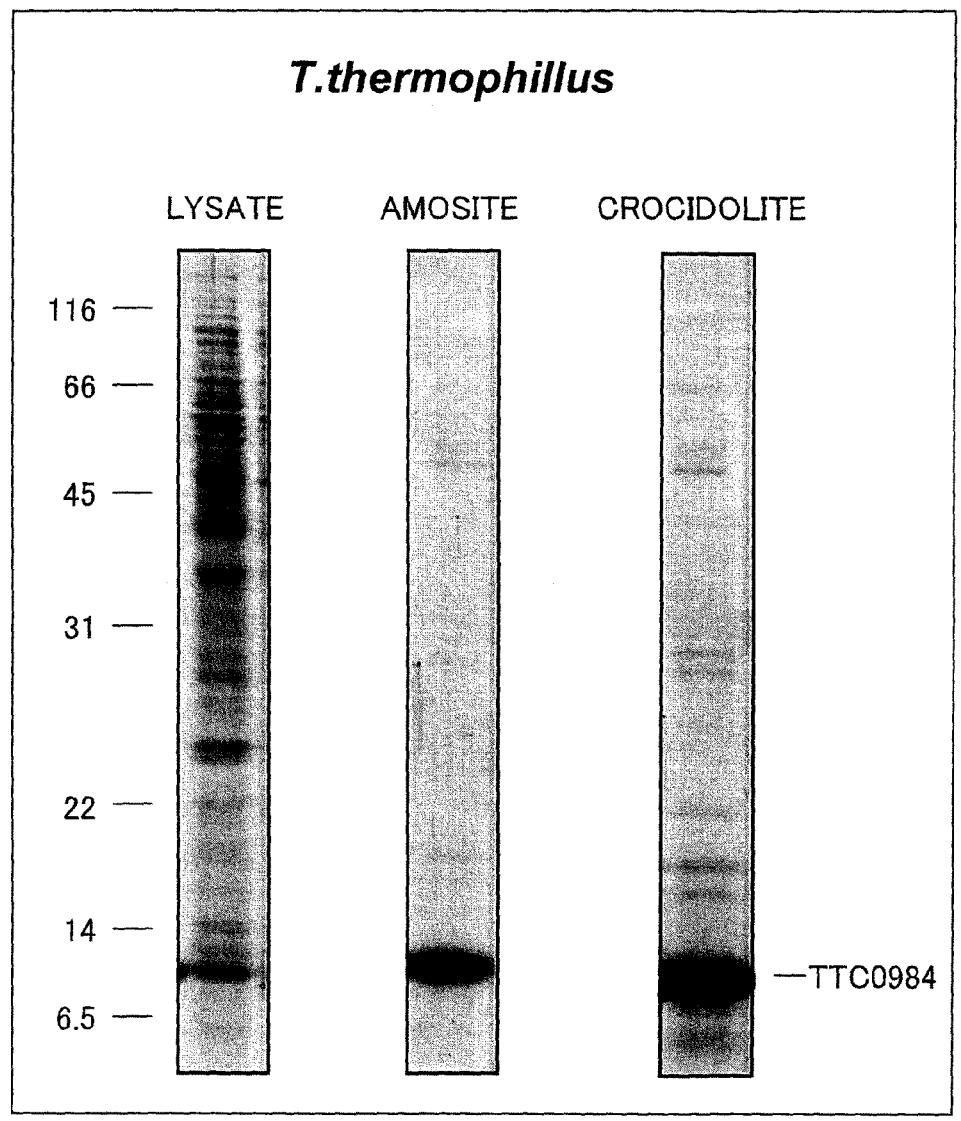
FIG. 10 is an electrophoretogram showing that an asbestos (crocidolite/amosite) binding protein was obtained from a cell lysate of highly thermophilic bacterium HB27.

FIG. 10 shows the result of polyacrylamide electrophoresis using highly thermophilic bacterium. As is apparent from FIG. 10, there was no difference between a band pattern of amosite and a band pattern of crocidolite, and a band of asbestos binding protein was found at the position corresponding to molecular weight of approximately 10 kD.

(4) Determination of Amino Acid Sequence and Base Sequence

An amino acid sequence of the protein binding to the above three types of asbestos (crocidolite/amosite) and base sequence of a gene encoding the asbestos binding protein were determined by a method as in Example 1.

It was revealed that *Escherichia coli* K12-derived asbestos binding protein having molecular weight of approximately 30 kD was a protein (ACCESSION: NP_415477) with an amino acid sequence represented by SEQ ID NO: 3, and a protein encoded by a gene (ompA) with a base sequence represented by SEQ ID NO: 4. The ompA is lower in molecular weight than the OmpA discovered in Example 1, which is considered to occur due to decomposition by endogenous protease in the ompA.

It was revealed that *Escherichia coli* K12-derived asbestos binding protein having molecular weight of approximately 40 kD was a protein (ACCESSION:NP_416719) with an amino acid sequence represented by SEQ ID NO: 5, and a protein encoded by a gene (ompC) with a base sequence represented by SEQ ID NO: 6.

It was revealed that highly thermophilic bacterium HB27-derived asbestos binding protein having molecular weight of approximately 10 kD was a protein (ACCESSION:YP_004953) with an amino acid sequence represented by SEQ ID NO: 25, and a protein encoded by a gene (ttc0984) with a base sequence represented by SEQ ID NO: 26.

(5) Construction of Expression Vector of TTC0984-AP Fusion Protein

Two types of oligonucleotide primers, P5: GGAATTC-CATATGGCTGCGAAGAAGACGGT (SEQ ID NO: 35) and P6: GTTGGATCCCCCTTCTTGACCTTATCCTTC (SEQ ID NO: 36), were produced based on a base sequence (SEQ ID NO: 26). PCR was performed with the oligonucleotide primers P5 and P6 by using a chromosome of highly thermophilic bacterium HB27 as a template. The reaction was performed using KOD Plus DNA polymerase (TOYOBO) according to TOYOBO's protocol. PCR products and the expression vector pET AP produced in Example 1 were treated with restriction enzymes NdeI and BamHI at 37° C. for 2 hours, and then subjected to agarose gel electrophoresis. Each of the respective DNA fragments cut out from gel was ligated with Ligation High (TOYOBO) at 16° C. for 2 hours, and then transformed into *Echerichia coli* MV1184. From the obtained colony, a plasmid into which the target DNA fragment was inserted was extracted. The plasmid was named as pET TTC0984-AP.

(6) Expression and Purification of TTC0984-AP Fusion Protein

Rosetta gamiB pLysS (Novagen) which had been transformed with the pET TTC0984-AP was cultured overnight at 37° C. in 2×YT medium. Then, 1% of the obtained cells was inoculated into another 2×YT medium. After the cells were cultured at 28° C. until OD600 reached 0.6, IPTG was added to the cultured cells so that a final concentration became 0.2 mM. Then, the resulting solution was cultured for 16 hours. After the cells were collected, a cell lysate was prepared by a method as in (2) of Example 1, and the cell lysate was purified by using a column of 1 ml of HisTrap HP (Amersham Bioscience). The cell lysate was washed with a buffer solution A (50 mM sodium phosphate having pH 7.4, 20% glycerose) containing 10 mM imidazole, and then eluted with the solution A containing 0.5M imidazole. A purification degree of the purified protein determined by polyacrylamide gel electrophoresis was more than 95%.

(7) Asbestos (Amosite) Detection Using Filter 1 mL of ultrapure water containing 1μ or 10μ gamosite (Japan Association for Working Environment Measurement) was filtered through DURAPORE MEMBRANE FILTERS (13 mm in diameter, 0.45 mm in pore diameter, MILLIPORE) by using a suction filtration apparatus (constructed by a filter holder, a suction bottle, and a pump). The filter was washed once with 1 ml of the above buffer solution, and the surface of the filter was covered with 50 μl of the above buffer solution containing 5 μg of purified TTC0984-AP protein. Then, the filter was reacted at room temperature for 1 minute. Further, the filter was washed with 1 ml of the above buffer solution three times. Thereafter, the surface of the filter was covered with 50 μl of coloring reagent (BCIP/NBT PLUS: Moss, INC.). Then, the filter was reacted at 37° C. for 10 minutes. After the reaction, the filter was dried and scanned by a scanner.

Figure 11:
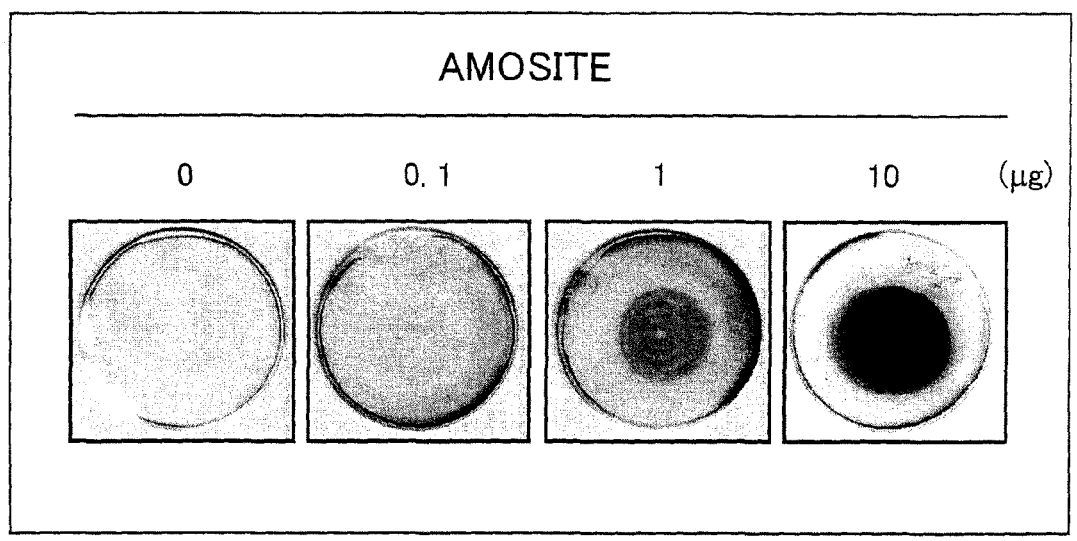
FIG. 11 is a view showing the result of asbestos (amosite) detection by using TTC0984-AP fusion protein and a filter.

FIG. 11 shows the result. As is apparent from FIG. 11, 1 μg of amosite was sufficiently detected by visual observation.

EXAMPLE 4

Detection of Asbestos in Building Material (1)

(1) Sample and Preparation of the Same

Figure 12:
FIG. 12 is a photograph of three types of building materials used as samples in Example 4.
Figure 12:
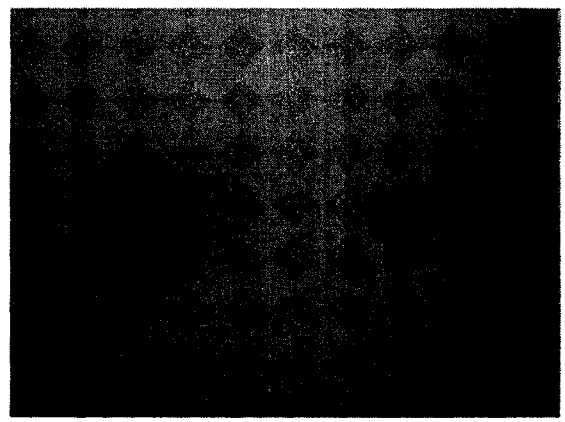
Figure 12:

Three types of building materials, which have been used in practice, were used as samples. FIG. 12 shows the three types of building materials as samples. It is recognized that no asbestos is contained in the three types of building materials.

The sample building materials were pulverized into powder by using a mortar, and 30 mg of building material was placed as a sample in each tube by weighing. Two tubes were prepared for each building material. To one of the two tubes, 300 μg (1% of sample) of chrysotile standard substance (Japan Association for Working Environment Measurement) was added.

(2) Operational Procedure

The operation was performed by the following procedural steps (a) through (f).

(a) Pre-Washing of Sample

To the sample prepared in (1) above and contained in the microtube, 1 ml of a buffer solution (25 mM Tris-HCl having pH 7.5, 0.5% Tween20) was added for mixing. Then, the mixture solution was subjected to centrifugation (10,000×g, 3 minutes) to precipitate the sample and remove the buffer solution.

(b) Blocking

To the sample was added 1 ml of blocking solution (solution obtained by addition of 0.5% casein to the buffer solution in (a)), and the resulting solution was mixed for 5 minutes by using a mixer (RVM-2000, manufactured by IWAKI Co., Ltd.). Then, the resulting solution was subjected to centrifugation (10,000×g, 3 minutes) to precipitate the sample and remove the blocking solution.

(c) Binding of Enzyme

To the sample was added 50 μl of DksA-AP cell lysate having protein concentration of 0.5 mg/ml, and the resulting solution was mixed for 5 minutes by using a mixer (T360, manufactured by TOMY SEIKO Co., Ltd.). Then, the resulting solution was subjected to centrifugation (10,000×g, 3 minutes) to precipitate the sample and remove extra enzyme solution.

(d) Washing

To the sample was added 1 ml of buffer solution in (a), and the resulting solution was subjected to centrifugation (10,000×g, 3 minutes) to precipitate the sample and remove the buffer solution. This operation was performed three times in total.

(e) Addition of Substrate

To the sample was added 50 μl of chromogenic solution (BCIP/NBT PLUS: Moss, INC.), and the resulting solution was mixed.

(f) Evaluation by Color

Color change in the solution was visually observed a given time period after addition of the substrate, to evaluate the presence or absence of asbestos.

(3) Result

Figure 13:
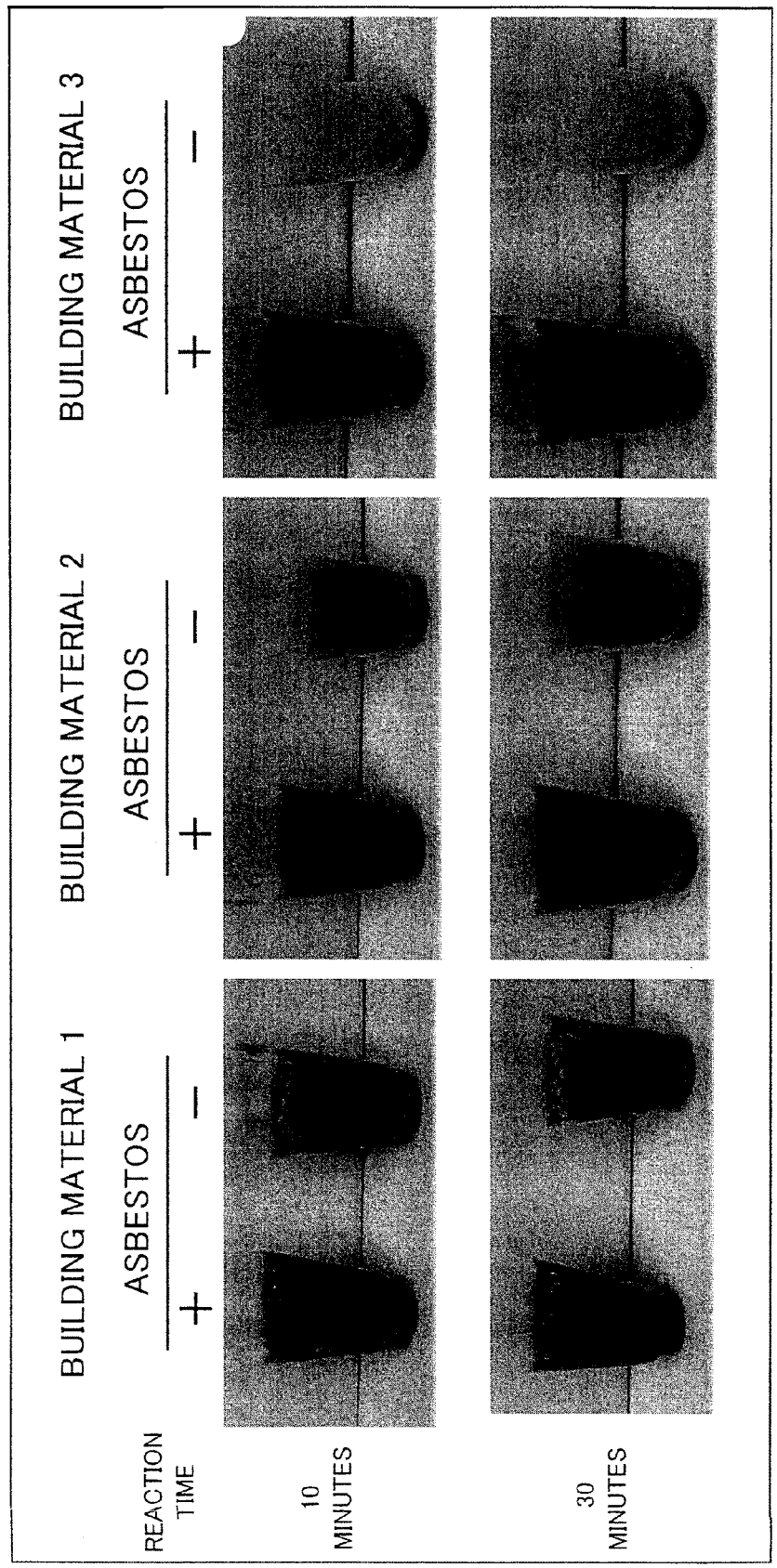
FIG. 13 is a view showing the result of detection of asbestos in building materials.

The result is shown in FIG. 13. As is apparent from FIG. 13, it was confirmed that as to three types of samples having 1% chrysotile added thereto, it is possible to sufficiently make visual evaluation on color changes in the reaction solution after 10-minute chromogenic reaction time. Even 30-minute chromogenic reaction time made clearer color change in the solution, without affecting the evaluation. Therefore, it is evident that a reaction time longer than 10 minutes is no problem.

EXAMPLE 5

Detection of Asbestos in Building Material (2)

As with asbestos, rock wool is made up of mineral fibers. However, rock wool is different from asbestos in that rock wool is made up of artificial mineral fibers while asbestos is made up of natural mineral fibers. Although rock wool containing asbestos is not currently on the market, such rockwool was on the market in the past. Therefore, a method by which the presence or absence of asbestos in rock wool can be easily detected is required. However, rock wool and asbestos, both of which are made up of mineral fibers, make it difficult to evaluate the presence or absence of asbestos in them by the conventional method using a phase microscope. In view of this, it was determined whether it is possible to distinguish between asbestos-containing rock wool and non-asbestos-containing rock wool by using a method according to the present invention.

Figure 14:
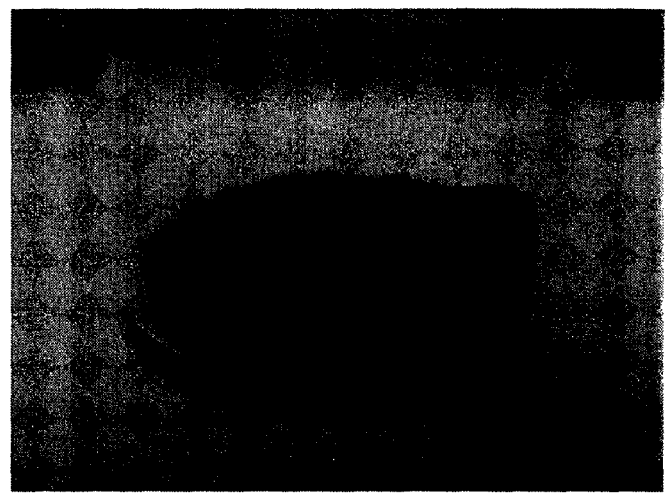
FIG. 14 is a photograph of rock wool used as a sample in Example 5.

FIG. 14 shows rock wool used as a sample.

To 30 mg of rock wool placed in each tube by weighing, 0 μg, 30 μg, 150 μg, and 300 μg of chrysotile standard substance (Japan Association for Working Environment Measurement) were added. As a result, these samples contain 0.1%, 0.5%, and 1.0% asbestos, respectively.

By using these samples, the operation was performed according to the procedural steps (a) through (f). Then, 10, 30, and 60 minutes after the addition of substrate, color changes were visually observed.

Figure 15:
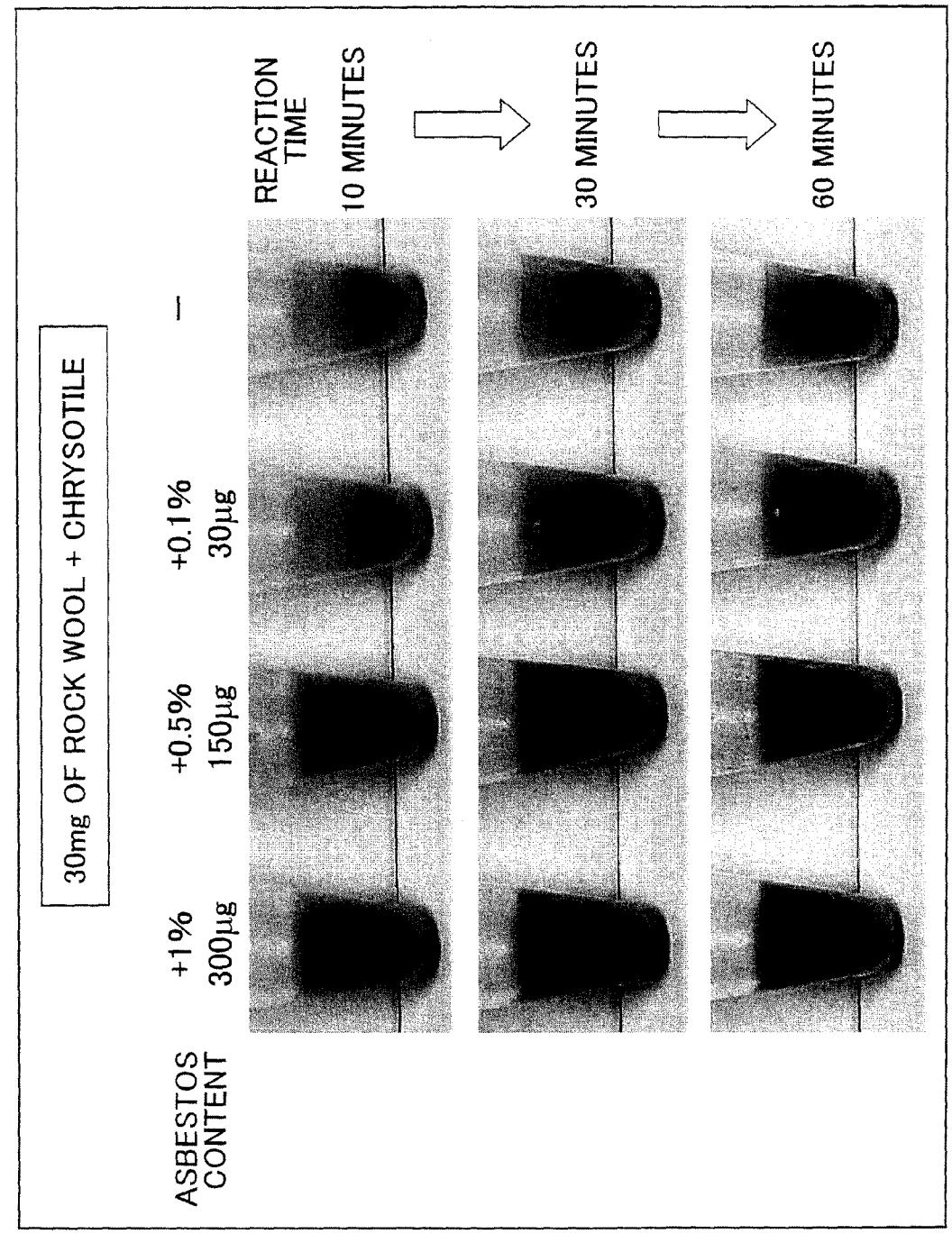
FIG. 15 is a view showing the result of detection of asbestos contained in rock wool.

The result is shown in FIG. 15. As is apparent from FIG. 15, it was confirmed that as to rock wool containing 0.5% or more asbestos, it is possible to sufficiently make visual evaluation on color changes in the reaction solution after 10-minute chromogenic reaction time. Even 30-minute or 60-minute chromogenic reaction time made clearer color changes in the solution, without affecting the evaluation. Therefore, it is evident that a reaction time longer than 10 minutes is no problem.

EXAMPLE 6

Easy Detection of Asbestos in Building Material (1) Sample and Preparation of the Same Sample preparation for experiment was performed by the following method. Samples as used were rock wool only (5 mg) and a mixture of 4 mg of rock wool and 1 mg of chrysotile standard substance (Japan Association for Working Environment Measurement).

(2) Operational Procedure

The operation was performed by the following procedural steps (a) through (f).

(a) Fixing of Samples

A trace amount (5 mg) of sample was applied and fixed by sticking onto a slide glass (manufactured by Matsunami Glass Ind., Ltd., 1 mm-thick MICRO SLIDE GLASS, white, ground edges) on which a double-sided adhesive tape was placed.

(b) Blocking

To the fixed sample was dropped 100 μl of blocking solution (solution obtained by addition of 0.5% casein to a buffer solution containing 25 mM Tris-HCl having pH 7.5, 0.5% Tween20), and the resulting solution was left at room temperature for 5 minutes. Then, the slide glass was immersed into 100 ml of water in a beaker for 1 minute to wash it and remove extra blocking agent. Thereafter, the slide glass was taken out of the beaker and left at room temperature for 5 minutes to dry it.

(c) Binding of Enzyme

To the sample was added 50 μl of DksA-AP cell lysate as in Example, and the resulting solution was left at room temperature for 5 minutes to bind enzyme to asbestos contained in the sample.

(d) Washing

The slide glass was immersed into 100 ml of water in a beaker for 1 minute and then taken out of the beaker. The slide glass was immersed into another water in a beaker for 1 minute. Such an operation was performed twice in total. Thereafter, the slide glass was taken out and left for 5 minutes to dry it.

(e) Addition of Substrate

To the sample was added 50 μl of chromogenic solution (BCIP/NBT PLUS: Moss, INC.), and the resulting solution was reacted at room temperature.

(f) Evaluation by Color

Color change in the solution was visually observed a given time period after addition of the substrate, to evaluate the presence or absence of asbestos.

(3) Result

Figure 16:
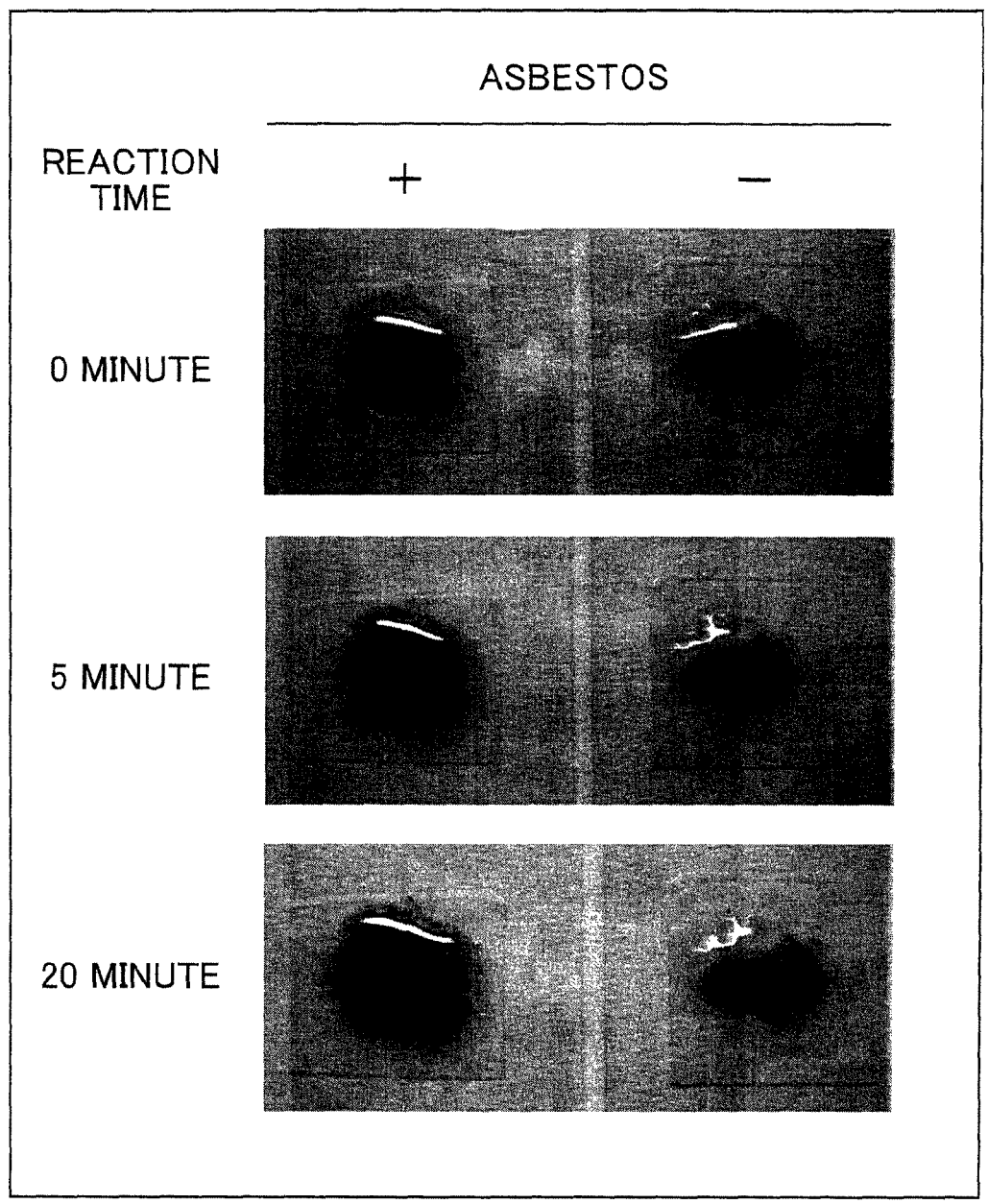
FIG. 16 is a view showing the result of detection of asbestos contained in rock wool on the slide glass.

The result is shown in FIG. 16. As is apparent from FIG. 16, the substrate dropped onto the sample containing chrysotile turned purple in appropriately 5 minutes, whereas no color change in the substrate dropped onto the sample not containing chrysotile was found. This result conforms the effectiveness of the method of the present invention. Even 20-minute reaction time made clearer color change, without affecting the evaluation. Therefore, it is evident that a reaction time longer than 5 minutes is no problem.

EXAMPLE 7

Detection of Asbestos Using Fluorescence Microscope (1) Construction of Expression Vector of DksA-GFP Fusion Protein In Example 7, phoA gene of the expression vector pET DksA-AP produced in Example 1 was substituted with gfp gene to produce an expression vector of DksA-GFP fusion protein. That is, two types of oligonucleotide primers, P7: AGAAAAGCTTAGTAAAGGAGAAGAACTTTTCACT (SEQ ID NO: 37) and P8: TCATGCGGCCGCAAGCT-CATCCATGCCATGTGTA (SEQ ID NO: 38), were produced based on a known gfp gene sequence (ACCESSION No. U62636: cloning vector pGFVuv). PCR was performed with the oligonucleotide primers P7 and P8 by using pGFPuv vector (clontech) as a template. The reaction was performed using KOD Plus DNA polymerase (TOYOBO) according to TOYOBO's protocol. PCR products and pET DksA-AP were treated with restriction enzymes NotI and HindIII at 37° C. for 2 hours, and then subjected to agarose gel electrophoresis. Each of the respective DNA fragments cut out from gel was ligated with Ligation High (TOYOBO) at 16° C. for 2 hours, and then transformed into *Echerichia coli* MV1184. From the obtained colony, a plasmid into which the target DNA fragment was inserted was extracted. The plasmid was named as pET DksA-GFP.

(2) Expression and Purification of DksA-GFP Fusion Protein

Rosetta BL21 (DE3) pLysS (Novagen) which had been transformed with the pET DksA-GFP was cultured overnight at 37° C. in 2×YT medium. Then, 1% of the obtained cells was inoculated into another 2×YT medium. After the cells were cultured at 28° C. until OD600 reached 0.6, IPTG was added to the cultured cells so that a final concentration became 0.3 mM. Then, the resulting solution was cultured for 16 hours. After the cells were collected, a cell lysate was prepared by a method as in (6) of Example 3, and the cell lysate was purified by affinity column. A purification degree of the purified protein determined by polyacrylamide gel electrophoresis was more than 95%.

(3) Fluorescence Detection of Chrysotile Using DksA-GFP 0.2 µg of purified DksA-GFP and 40 µg of chrysotile (white asbestos, Japan Association for Working Environment Measurement) were mixed in 10 µl of buffer solution (25 mM Tris-HCl having pH 7.5, 0.5% Tween20), and the mixture solution was left at room temperature for 10 minutes for binding. After the binding, 3 µl of sample was dropped onto a slide glass (Matsunami Glass Ind., Ltd., 1 mm-thick MICRO SLIDE GLASS, white, ground edges), and observed through an incident-light fluorescence microscope BX-60 (OLYMPUS). For fluorescence observation of GFP, U-MNIBA cube (dichroic mirror: DM505, excitation filter: BP470-490, absorption filter: BA515IF) was used. For image capturing, microscope digital camera DP70 (OLYMPUS) was used.

Figure 17:
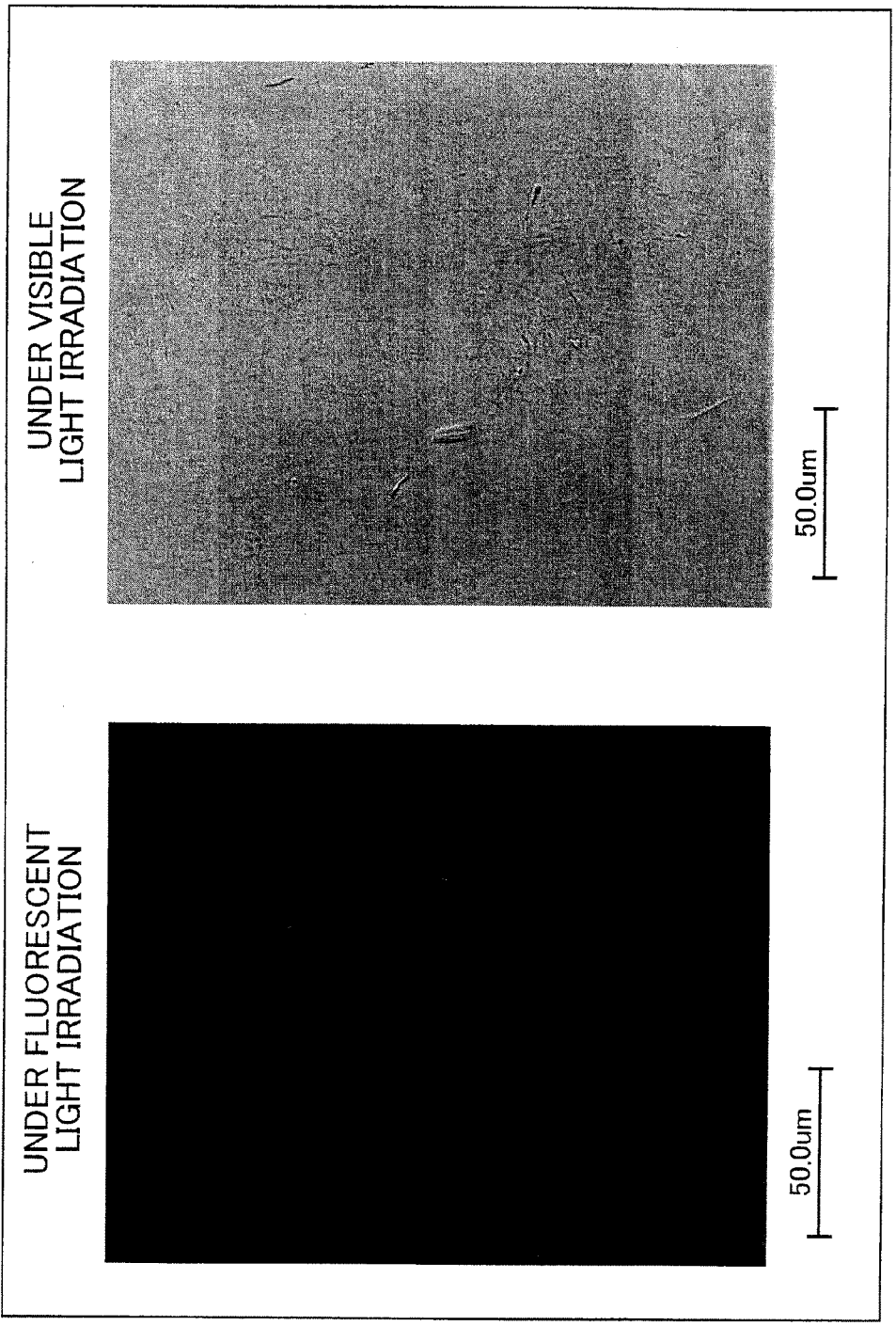
FIG. 17 is an image showing the result of detection of asbestos through a fluorescence microscope by using DksA-GFP fusion protein.

The result is shown in FIG. 17. As is apparent from FIG. 17, it was possible to observe, under fluorescent light irradiation, chrysotile fibers which can be seen under visible light irradiation. In addition, it was possible to observe, under fluorescent light irradiation, fibers which are difficult to see by naked eyes under visible light irradiation, although it is unclear in FIG. 17.

Specific embodiments or examples implemented in BEST MODE FOR CARRYING OUT THE INVENTION only show technical features of the present invention and are not intended to limit the scope of the invention. Variations can be effected within the spirit of the present invention and the scope of the following claims.

Further, all of the academic documents and patent documents listed herein are incorporated by reference herein.

Industrial Applicability

The present invention is applicable to fields including public sanitation, environmental sanitation, and medical treatment. Furthermore, the present invention is applicable to fields including pharmaceutical industry and basic medical science.

---

The invention claimed is:

1. An asbestos detection method comprising:
a step of bringing a protein, capable of binding to asbestos in a solution containing at least 0.1 M or more sodium chloride, into contact with asbestos in a sample; and
a step of detecting the protein binding to the asbestos,
wherein the protein consists of an amino acid sequence selected from the group consisting of SEQ ID NOs: 1, 3, 5, 7, 9, 11, 13, 15, 17, 19, and 25.

2. An asbestos detection method comprising:
a step of obtaining a fusion protein, wherein the fusion protein comprises (i) a protein, capable of binding to asbestos in a solution containing at least 0.1 M or more sodium chloride, and (ii) a reporter protein;
a step of bringing the obtained fusion protein into contact with asbestos in a sample; and
a step of detecting the fusion protein binding to the asbestos,
wherein the protein, capable of binding to asbestos in a solution containing at least 0.1 M or more sodium chloride, consists of an amino acid sequence selected from the group consisting of SEQ ID NOs: 1, 3, 5, 7, 9, 11, 13, 15, 17, 19, and 25.

3. The asbestos detection method according to claim 2, wherein
the reporter protein is a protein selected from the group consisting of: fluorescent protein, luciferase, alkaline phosphatase, beta galactosidase, diaphorase, and peroxidase.

4. The asbestos detection method according to claim 1, wherein the protein capable of binding to asbestos is labeled with a fluorescent material.

5. The asbestos detection method according to claim 4, wherein the fluorescent material is Cy3, Cy5, or Fluorescein.

* * * * *

SEQUENCE LISTING

<160> NUMBER OF SEQ ID NOS: 38

<210> SEQ ID NO 1
<211> LENGTH: 638
<212> TYPE: PRT
<213> ORGANISM: Escherichia coli

<400> SEQUENCE: 1

```
Met Gly Lys Ile Ile Gly Ile Asp Leu Gly Thr Thr Asn Ser Cys Val
  1               5                  10                  15

Ala Ile Met Asp Gly Thr Thr Pro Arg Val Leu Glu Asn Ala Glu Gly
             20                  25                  30

Asp Arg Thr Thr Pro Ser Ile Ile Ala Tyr Thr Gln Asp Gly Glu Thr
         35                  40                  45

Leu Val Gly Gln Pro Ala Lys Arg Gln Ala Val Thr Asn Pro Gln Asn
     50                  55                  60

Thr Leu Phe Ala Ile Lys Arg Leu Ile Gly Arg Arg Phe Gln Asp Glu
 65                  70                  75                  80

Glu Val Gln Arg Asp Val Ser Ile Met Pro Phe Lys Ile Ile Ala Ala
                 85                  90                  95
```

```
Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
            115                 120                 125

Asp Tyr Leu Gly Glu Pro Val Thr Glu Ala Val Ile Thr Val Pro Ala
            130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
            165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
            195                 200                 205

Glu Val Asp Gly Glu Lys Thr Phe Glu Val Leu Ala Thr Asn Gly Asp
            210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
            245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
            275                 280                 285

Asp Ala Thr Gly Pro Lys His Met Asn Ile Lys Val Thr Arg Ala Lys
            290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
            325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
            355                 360                 365

Glu Ala Val Ala Ile Gly Ala Ala Val Gln Gly Gly Val Leu Thr Gly
            370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
            405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
            435                 440                 445

Ala Asp Asn Lys Ser Leu Gly Gln Phe Asn Leu Asp Gly Ile Asn Pro
            450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
            485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
            515                 520                 525
```

```
Phe Glu Glu Leu Val Gln Thr Arg Asn Gln Gly Asp His Leu Leu His
    530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
                580                 585                 590

Gln Val Ser Gln Lys Leu Met Glu Ile Ala Gln Gln His Ala Gln
        595                 600                 605

Gln Gln Thr Ala Gly Ala Asp Ala Ser Ala Asn Asn Ala Lys Asp Asp
    610                 615                 620

Asp Val Val Asp Ala Glu Phe Glu Glu Val Lys Asp Lys Lys
625                 630                 635
```

<210> SEQ ID NO 2
<211> LENGTH: 1917
<212> TYPE: DNA
<213> ORGANISM: Escherichia coli

<400> SEQUENCE: 2

```
atgggtaaaa taattggtat cgacctgggt actaccaact cttgtgtagc gattatggat      60
ggcaccactc ctcgcgtgct ggagaacgcc gaaggcgatc gcaccacgcc ttctatcatt     120
gcctataccc aggatggtga aactctagtt ggtcagccgg ctaaacgtca ggcagtgacg     180
aacccgcaaa acactctgtt tgcgattaaa cgcctgattg gtcgccgctt ccaggacgaa     240
gaagtacagc gtgatgtttc catcatgccg ttcaaaatta ttgctgctga taacggcgac     300
gcatgggtcg aagttaaagg ccagaaaatg gcaccgccgc agatttctgc tgaagtgctg     360
aaaaaaatga agaaaaccgc tgaagattac ctgggtgaac cggtaactga agctgttatc     420
accgtaccgg catactttaa cgatgctcag cgtcaggcaa ccaaagacgc aggccgtatc     480
gctggtctgg aagtaaaacg tatcatcaac gaaccgaccg cagctgcgct ggcttacggt     540
ctggacaaag cactggcaa ccgtactatc gcggtttatg acctgggtgg tggtacttc      600
gatatttcta ttatcgaaat cgacgaagtt gacggcgaaa aaaccttcga agttctggca     660
accaacggtg ataccacct gggggggtgaa gacttcgaca ccgtctgat caactatctg     720
gttgaagaat tcaagaaaga tcagggcatt gacctgcgca cgatccgct ggcaatgcag     780
cgcctgaaaa agcggcaga aaagcgaaa atcgaactgt cttccgctca gcagaccgac     840
gttaacctgc catacatcac tgcagacgcg accggtccga acacatgaa catcaaagtg     900
actcgtgcga aactggaaag cctggttgaa gatctggtaa accgttccat tgagccgctg     960
aaagttgcac tgcaggacgc tggcctgtcc gtatctgata tcgacgacgt tatcctcgtt    1020
ggtggtcaga ctcgtatgcc aatggttcag aagaaagttg ctgagttctt tggtaaagag    1080
ccgcgtaaag acgttaaccc ggacgaagct gtagcaatcg gtgctgctgt tcagggtggt    1140
gttctgactg gtgacgtaaa agacgtactg ctgctggacg ttacccgct gtctctgggt    1200
atcgaaacca tgggcggtgt gatgacgacg ctgatcgcga aaacaccac tatcccgacc    1260
aagcacagcc aggtgttctc taccgctgaa gacaaccagt ctgcggtaac catccatgtg    1320
ctgcagggtg aacgtaaacg tgcggctgat aacaaatctc tgggtcagtt caacctagat    1380
ggtatcaacc cggcaccgcg cggcatgccg cagatcgaag ttaccttcga tatcgatgct    1440
gacggtatcc tgcacgtttc cgcgaaagat aaaaacagcg gtaaagagca aagatcacc    1500
```

-continued

```
atcaaggctt cttctggtct gaacgaagat gaaatccaga aaatggtacg cgacgcagaa    1560
gctaacgccg aagctgaccg taagtttgaa gagctggtac agactcgcaa ccagggcgac    1620
catctgctgc acagcacccg taagcaggtt gaagaagcag gcgacaaact gccggctgac    1680
gacaaaactg ctatcgagtc tgcgctgact gcactggaaa ctgctctgaa aggtgaagac    1740
aaagccgcta tcgaagcgaa atgcaggaa ctggcacagg tttcccagaa actgatggaa    1800
atcgcccagc agcaacatgc ccagcagcag actgccggtg ctgatgcttc tgcaaacaac    1860
gcgaaagatg acgatgttgt cgacgctgaa tttgaagaag tcaaagacaa aaataa       1917
```

<210> SEQ ID NO 3
<211> LENGTH: 346
<212> TYPE: PRT
<213> ORGANISM: Escherichia coli

<400> SEQUENCE: 3

```
Met Lys Lys Thr Ala Ile Ala Ile Ala Val Ala Leu Ala Gly Phe Ala
  1               5                  10                  15

Thr Val Ala Gln Ala Ala Pro Lys Asp Asn Thr Trp Tyr Thr Gly Ala
             20                  25                  30

Lys Leu Gly Trp Ser Gln Tyr His Asp Thr Gly Phe Ile Asn Asn Asn
         35                  40                  45

Gly Pro Thr His Glu Asn Gln Leu Gly Ala Gly Ala Phe Gly Gly Tyr
     50                  55                  60

Gln Val Asn Pro Tyr Val Gly Phe Glu Met Gly Tyr Asp Trp Leu Gly
 65                  70                  75                  80

Arg Met Pro Tyr Lys Gly Ser Val Glu Asn Gly Ala Tyr Lys Ala Gln
                 85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
    130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
        195                 200                 205

Glu Val Gln Thr Lys His Phe Thr Leu Lys Ser Asp Val Leu Phe Asn
    210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
    290                 295                 300

Pro Val Thr Gly Asn Thr Cys Asp Asn Val Lys Gln Arg Ala Ala Leu
```

Ile Asp Cys Leu Ala Pro Asp Arg Arg Val Glu Ile Glu Val Lys Gly
305                 310                 315                 320

Ile Lys Asp Val Val Thr Gln Pro Gln Ala
            325                 330                 335

340                 345

<210> SEQ ID NO 4
<211> LENGTH: 1041
<212> TYPE: DNA
<213> ORGANISM: Escherichia coli

<400> SEQUENCE: 4
atgaaaaaga cagctatcgc gattgcagtg gcactggctg gtttcgctac cgtagcgcag      60
gccgctccga agataacac ctggtacact ggtgctaaac tgggctggtc ccagtaccat     120
gacactggtt tcatcaacaa caatggcccg acccatgaaa accaactggg cgctggtgct     180
tttggtggtt accaggttaa cccgtatgtt ggctttgaaa tgggttacga ctggttaggt     240
cgtatgccgt acaaaggcag cgttgaaaac ggtgcataca agctcaggg cgttcaactg      300 accgctaaac tgggttaccc aatcactgac gacctggaca tctacactcg tctgggtggc     360
atggtatggc gtgcagacac taaatccaac gtttatggta aaaccacga caccggcgtt     420 tctccggtct tcgctggcgg tgttgagtac gcgatcactc tgaaatcgc tacccgtctg     480 gaataccagt ggaccaacaa catcggtgac gcacacacca tcggcactcg tccggacaac     540
ggcatgctga cctgggtgt ttcctaccgt ttcggtcagg gcgaagcagc tccagtagtt     600
gctccggctc cagctccggc accggaagta cagaccaagc acttcactct gaagtctgac     660
gttctgttca acttcaacaa agcaaccctg aaaccggaag tcaggctgc tctggatcag     720 ctgtacagcc agctgagcaa cctggatccg aaagacggtt ccgtagttgt tctgggttac     780
accgaccgca tcggttctga cgcttacaac cagggtctgt ccgagcgccg tgctcagtct     840
gttgttgatt acctgatctc caaaggtatc ccggcagaca gatctccgc acgtggtatg     900 ggcgaatcca acccggttac tgcaacacc tgtgacaacg tgaaacagcg tgctgcactg     960
atcgactgcc tggctccgga tcgtcgcgta gagatcgaag ttaaaggtat caaagacgtt    1020
gtaactcagc cgcaggctta a                                             1041

<210> SEQ ID NO 5
<211> LENGTH: 367
<212> TYPE: PRT
<213> ORGANISM: Escherichia coli

<400> SEQUENCE: 5

Met Lys Val Lys Val Leu Ser Leu Leu Val Pro Ala Leu Leu Val Ala
  1               5                  10                  15

Gly Ala Ala Asn Ala Ala Glu Val Tyr Asn Lys Asp Gly Asn Lys Leu
                20                  25                  30

Asp Leu Tyr Gly Lys Val Asp Gly Leu His Tyr Phe Ser Asp Asn Lys
            35                  40                  45

Asp Val Asp Gly Asp Gln Thr Tyr Met Arg Leu Gly Phe Lys Gly Glu
        50                  55                  60

Thr Gln Val Thr Asp Gln Leu Thr Gly Tyr Gly Gln Trp Glu Tyr Gln
    65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

```
Arg Asn Tyr Gly Val Val Tyr Asp Val Thr Ser Trp Thr Asp Val Leu
        115                 120                 125
Pro Glu Phe Gly Gly Asp Thr Tyr Gly Ser Asp Asn Phe Met Gln Gln
    130                 135                 140
Arg Gly Asn Gly Phe Ala Thr Tyr Arg Asn Thr Asp Phe Phe Gly Leu
145                 150                 155                 160
Val Asp Gly Leu Asn Phe Ala Val Gln Tyr Gln Gly Lys Asn Gly Asn
                165                 170                 175
Pro Ser Gly Glu Gly Phe Thr Ser Gly Val Thr Asn Asn Gly Arg Asp
            180                 185                 190
Ala Leu Arg Gln Asn Gly Asp Gly Val Gly Gly Ser Ile Thr Tyr Asp
        195                 200                 205
Tyr Glu Gly Phe Gly Ile Gly Gly Ala Ile Ser Ser Lys Arg Thr
    210                 215                 220
Asp Ala Gln Asn Thr Ala Ala Tyr Ile Gly Asn Gly Asp Arg Ala Glu
225                 230                 235                 240
Thr Tyr Thr Gly Gly Leu Lys Tyr Asp Ala Asn Asn Ile Tyr Leu Ala
                245                 250                 255
Ala Gln Tyr Thr Gln Thr Tyr Asn Ala Thr Arg Val Gly Ser Leu Gly
            260                 265                 270
Trp Ala Asn Lys Ala Gln Asn Phe Glu Ala Val Ala Gln Tyr Gln Phe
        275                 280                 285
Asp Phe Gly Leu Arg Pro Ser Leu Ala Tyr Leu Gln Ser Lys Gly Lys
    290                 295                 300
Asn Leu Gly Arg Gly Tyr Asp Asp Glu Asp Ile Leu Lys Tyr Val Asp
305                 310                 315                 320
Val Gly Ala Thr Tyr Tyr Phe Asn Lys Asn Met Ser Thr Tyr Val Asp
                325                 330                 335
Tyr Lys Ile Asn Leu Leu Asp Asp Asn Gln Phe Thr Arg Asp Ala Gly
            340                 345                 350
Ile Asn Thr Asp Asn Ile Val Ala Leu Gly Leu Val Tyr Gln Phe
        355                 360                 365

<210> SEQ ID NO 6
<211> LENGTH: 1104
<212> TYPE: DNA
<213> ORGANISM: Escherichia coli

<400> SEQUENCE: 6
atgaaagtta aagtactgtc cctcctggtc ccagctctgc tggtagcagg cgcagcaaac      60
gctgctgaag tttacaacaa agacggcaac aaattagatc tgtacggtaa agtagacggc     120
ctgcactatt tctctgacaa caaagatgta gatggcgacc agacctacat gcgtcttggc     180
ttcaaaggtg aaactcaggt tactgaccag ctgaccggtt acggccagtg gaatatcag      240 atccagggca acagcgctga aaacgaaaac aactcctgga cccgtgtggc attcgcaggt     300
ctgaaattcc aggatgtggg ttctttcgac tacggtcgta actacggcgt tgtttatgac     360
gtaacttcct ggaccgacgt actgccagaa ttcggtggtg acacctacgg ttctgacaac     420
ttcatgcagc agcgtggtaa cggcttcgcg acctaccgta acactgactt cttcggtctg     480
gttgacggcc tgaactttgc tgttcagtac cagggtaaaa acgcaaccc atctggtgaa      540 ggctttacta gtggcgtaac taacaacggt cgtgacgcac tgcgtcaaaa cggcgacggc     600
gtcggcggtt ctatcactta tgattacgaa ggtttcggta tcggtggtgc gatctccagc     660
tccaaacgta ctgatgctca gaacaccgct gcttacatcg gtaacggcga ccgtgctgaa     720
```

```
acctacactg gtggtctgaa atacgacgct aacaacatct acctggctgc tcagtacacc    780
cagacctaca acgcaactcg cgtaggttcc ctgggttggg cgaacaaagc acagaacttc    840
gaagctgttg ctcagtacca gttcgacttc ggtctgcgtc cgtccctggc ttacctgcag    900
tctaaaggta aaacctggg tcgtggctac gacgacgaag atatcctgaa atatgttgat    960
gttggtgcta cctactactt caacaaaaac atgtccacct acgttgacta caaaatcaac   1020
ctgctggacg acaaccagtt cactcgtgac gctggcatca acactgataa catcgtagct   1080
ctgggtctgg tttaccagtt ctaa                                         1104
```

<210> SEQ ID NO 7
<211> LENGTH: 161
<212> TYPE: PRT
<213> ORGANISM: Escherichia coli

<400> SEQUENCE: 7

```
Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys
```

<210> SEQ ID NO 8
<211> LENGTH: 486
<212> TYPE: DNA
<213> ORGANISM: Escherichia coli

<400> SEQUENCE: 8

```
gtgaaaaagt ggttattagc tgcaggtctc ggtttagcac tggcaacttc tgctcaggcg     60
gctgacaaaa ttgcaatcgt caacatgggc agcctgttcc agcaggtagc gcagaaaacc    120
ggtgtttcta acacgctgga aaatgagttc aaaggccgtg ccagcgaact gcagcgtatg    180
gaaaccgatc tgcaggctaa aatgaaaaag ctgcagtcca tgaaagcggg cagcgatcgc    240
actaagctgg aaaagacgt gatggctcag cgccagactt tgctcagaa agcgcaggct    300 tttgagcagg atcgcgcacg tcgttccaac gaagaacgcg gcaaactggt tactcgtatc    360
cagactgctg tgaaatccgt tgccaacagc caggatatcg atctggttgt tgatgcaaac    420
gccgttgctt acaacagcag cgatgtaaaa gacatcactg ccgacgtact gaaacaggtt    480
aaataa                                                               486
```

<210> SEQ ID NO 9
<211> LENGTH: 130
<212> TYPE: PRT
<213> ORGANISM: Escherichia coli

<400> SEQUENCE: 9

Met Lys Lys Phe Ala Ala Val Ile Ala Val Met Ala Leu Cys Ser Ala
1               5                   10                  15

Pro Val Met Ala Ala Glu Gln Gly Gly Phe Ser Gly Pro Ser Ala Thr
            20                  25                  30

Gln Ser Gln Ala Gly Gly Phe Gln Gly Pro Asn Gly Ser Val Thr Thr
        35                  40                  45

Val Glu Ser Ala Lys Ser Leu Arg Asp Asp Thr Trp Val Thr Leu Arg
    50                  55                  60

Gly Asn Ile Val Glu Arg Ile Ser Asp Asp Leu Tyr Val Phe Lys Asp
65                  70                  75                  80

Ala Ser Gly Thr Ile Asn Val Asp Ile Asp His Lys Arg Trp Asn Gly
                85                  90                  95

Val Thr Val Thr Pro Lys Asp Thr Val Glu Ile Gln Gly Glu Val Asp
            100                 105                 110

Lys Asp Trp Asn Ser Val Glu Ile Asp Val Lys Gln Ile Arg Lys Val
        115                 120                 125

Asn Pro
    130

<210> SEQ ID NO 10
<211> LENGTH: 393
<212> TYPE: DNA
<213> ORGANISM: Escherichia coli

<400> SEQUENCE: 10
atgaaaaaat tcgcagcagt aatcgcagta atggccctgt gcagcgcacc ggtgatggca      60
gcagagcagg gcggtttttc tggcccatcg gcaacgcaaa gtcaggccgg aggattccag     120
gggccgaacg gcagcgtaac gactgtagaa agcgcaaaat ccctgcgtga cgacacctgg     180
gtaaccctgc gcggcaatat cgttgaacgc atctctgacg atctctacgt gttcaaagat     240
gccagcggta ctatcaatgt tgatatcgac cacaaacgct ggaacggcgt gacggtgacg     300
ccgaaagata cggttgagat tcagggtgaa gtcgataaag actggaattc tgttgaaatt     360
gacgtcaaac agatccgcaa agtaaatccg taa                                  393

<210> SEQ ID NO 11
<211> LENGTH: 151
<212> TYPE: PRT
<213> ORGANISM: Escherichia coli

<400> SEQUENCE: 11

Met Gln Glu Gly Gln Asn Arg Lys Thr Ser Ser Leu Ser Ile Leu Ala
1               5                   10                  15

Ile Ala Gly Val Glu Pro Tyr Gln Glu Lys Pro Gly Glu Glu Tyr Met
            20                  25                  30

Asn Glu Ala Gln Leu Ala His Phe Arg Arg Ile Leu Glu Ala Trp Arg
        35                  40                  45

Asn Gln Leu Arg Asp Glu Val Asp Arg Thr Val Thr His Met Gln Asp
    50                  55                  60

Glu Ala Ala Asn Phe Pro Asp Pro Val Asp Arg Ala Ala Gln Glu Glu
65                  70                  75                  80

```
Glu Phe Ser Leu Glu Leu Arg Asn Arg Asp Arg Glu Arg Lys Leu Ile
                85                  90                  95

Lys Lys Ile Glu Lys Thr Leu Lys Lys Val Glu Asp Glu Asp Phe Gly
            100                 105                 110

Tyr Cys Glu Ser Cys Gly Val Glu Ile Gly Ile Arg Arg Leu Glu Ala
        115                 120                 125

Arg Pro Thr Ala Asp Leu Cys Ile Asp Cys Lys Thr Leu Ala Glu Ile
130                 135                 140

Arg Glu Lys Gln Met Ala Gly
145                 150

<210> SEQ ID NO 12
<211> LENGTH: 456
<212> TYPE: DNA
<213> ORGANISM: Escherichia coli

<400> SEQUENCE: 12
atgcaagaag ggcaaaaccg taaaacatcg tccctgagta ttctcgccat cgctggggtg      60
gaaccatatc aggagaagcc gggcgaagag tatatgaatg aagcccagct ggcgcacttc     120
cgtcgtattc tggaagcatg gcgtaatcaa ctcagggatg aagtcgatcg caccgttaca     180
catatgcagg atgaagcagc caacttcccg gaccccggtag accgtgcagc ccaggaagaa     240
gagttcagcc tcgaactgcg taaccgcgat cgcgagcgta agctgatcaa aaagatcgag     300
aagacgctga aaaagtggga agacgaagat ttcggctact gcgaatcctg cggtgttgaa     360
attggtattc gccgtctgga agcgcgcccg acagccgatc tgtgcatcga ctgcaaaacg     420
ctggctgaaa ttcgcgaaaa acagatggct ggctaa                                456

<210> SEQ ID NO 13
<211> LENGTH: 137
<212> TYPE: PRT
<213> ORGANISM: Escherichia coli

<400> SEQUENCE: 13

Met Ser Glu Ala Leu Lys Ile Leu Asn Asn Ile Arg Thr Leu Arg Ala
1               5                   10                  15

Gln Ala Arg Glu Cys Thr Leu Glu Thr Leu Glu Glu Met Leu Glu Lys
            20                  25                  30

Leu Glu Val Val Val Asn Glu Arg Arg Glu Glu Ser Ala Ala Ala
        35                  40                  45

Ala Glu Val Glu Glu Arg Thr Arg Lys Leu Gln Gln Tyr Arg Glu Met
    50                  55                  60

Leu Ile Ala Asp Gly Ile Asp Pro Asn Glu Leu Leu Asn Ser Leu Ala
65                  70                  75                  80

Ala Val Lys Ser Gly Thr Lys Ala Lys Arg Ala Gln Arg Pro Ala Lys
                85                  90                  95

Tyr Ser Tyr Val Asp Glu Asn Gly Glu Thr Lys Thr Trp Thr Gly Gln
            100                 105                 110

Gly Arg Thr Pro Ala Val Ile Lys Lys Ala Met Asp Glu Gln Gly Lys
        115                 120                 125

Ser Leu Asp Asp Phe Leu Ile Lys Gln
    130                 135

<210> SEQ ID NO 14
<211> LENGTH: 414
<212> TYPE: DNA
<213> ORGANISM: Escherichia coli
```

<400> SEQUENCE: 14

```
atgagcgaag cacttaaaat tctgaacaac atccgtactc ttcgtgcgca ggcaagagaa      60
tgtacacttg aaacgctgga agaaatgctg gaaaaattag aagttgttgt taacgaacgt     120
cgcgaagaag aaagcgcggc tgctgctgaa gttgaagagc gcactcgtaa actgcagcaa     180
tatcgcgaaa tgctgatcgc tgacggtatt gacccgaacg aactgctgaa tagccttgct     240
gccgttaaat ctggcaccaa agctaaacgt gctcagcgtc cggcaaaata tagctacgtt     300
gacgaaaacg gcgaaactaa aacctggact ggccaaggcc gtactccagc tgtaatcaaa     360
aaagcaatgg atgagcaagg taaatccctc gacgatttcc tgatcaagca ataa           414
```

<210> SEQ ID NO 15
<211> LENGTH: 70
<212> TYPE: PRT
<213> ORGANISM: Pseudomonas putida

<400> SEQUENCE: 15

Met Ser Asn Arg Gln Gln Gly Thr Val Lys Trp Phe Asn Asp Glu Lys
 1               5                  10                  15

Gly Tyr Gly Phe Ile Thr Pro Ala Gly Gly Asp Asp Leu Phe Val
            20                  25                  30

His Phe Lys Ala Ile Glu Ser Asp Gly Phe Lys Ser Leu Lys Glu Gly
        35                  40                  45

Gln Thr Val Ser Phe Val Ala Glu Arg Gly Gln Lys Gly Met Gln Ala
    50                  55                  60

Ala Gln Val Arg Pro Glu
65                  70

<210> SEQ ID NO 16
<211> LENGTH: 213
<212> TYPE: DNA
<213> ORGANISM: Pseudomonas putida

<400> SEQUENCE: 16

```
atgtccaatc gccaacaagg caccgtcaaa tggttcaatg atgagaaagg ctacggcttc      60
atcaccccag caggcggcgg cgacgacctg ttcgtacact tcaaagccat cgaatctgac     120
ggcttcaaga gcctgaaaga aggccagact gtttccttcg tcgccgagcg cggccagaag     180
ggcatgcagg ctgcacaggt tcgtccggag taa                                  213
```

<210> SEQ ID NO 17
<211> LENGTH: 425
<212> TYPE: PRT
<213> ORGANISM: Corynebacterium glutamicum

<400> SEQUENCE: 17

Met Ala Glu Ile Met His Val Phe Ala Arg Glu Ile Leu Asp Ser Arg
 1               5                  10                  15

Gly Asn Pro Thr Val Glu Ala Glu Val Phe Leu Asp Asp Gly Ser His
            20                  25                  30

Gly Val Ala Gly Val Pro Ser Gly Ala Ser Thr Gly Val His Glu Ala
        35                  40                  45

His Glu Leu Arg Asp Gly Asp Arg Tyr Leu Gly Lys Gly Val Leu
    50                  55                  60

Lys Ala Val Glu Asn Val Asn Glu Glu Ile Gly Asp Glu Leu Ala Gly
65                  70                  75                  80

Leu Glu Ala Asp Asp Gln Arg Leu Ile Asp Glu Ala Met Ile Lys Leu

|  | 85 |  |  |  | 90 |  |  |  | 95 |  |  |
|---|---|---|---|---|---|---|---|---|---|---|---|

Asp Gly Thr Ala Asn Lys Ser Arg Leu Gly Ala Asn Ala Ile Leu Gly
            100                  105              110

Val Ser Met Ala Val Ala Lys Ala Ala Asp Ser Ala Gly Leu Pro
115               120                 125

Leu Phe Arg Tyr Ile Gly Gly Pro Asn Ala His Val Leu Pro Val Pro
        130              135              140

Met Met Asn Ile Ile Asn Gly Gly Ala His Ala Asp Ser Gly Val Asp
145               150              155          160

Val Gln Glu Phe Met Ile Ala Pro Ile Gly Ala Glu Thr Phe Ser Glu
            165              170             175

Ala Leu Arg Asn Gly Ala Glu Val Tyr His Ala Leu Lys Ser Val Ile
        180              185             190

Lys Glu Lys Gly Leu Ser Thr Gly Leu Gly Asp Glu Gly Phe Ala
195               200              205

Pro Ser Val Gly Ser Thr Arg Glu Ala Leu Asp Leu Ile Val Glu Ala
        210              215             220

Ile Glu Lys Ala Gly Phe Thr Pro Gly Lys Asp Ile Ala Leu Ala Leu
225               230              235          240

Asp Val Ala Ser Ser Glu Phe Phe Lys Asp Gly Thr Tyr His Phe Glu
        245              250             255

Gly Gly Gln His Ser Ala Ala Glu Met Ala Asn Val Tyr Ala Glu Leu
        260              265             270

Val Asp Ala Tyr Pro Ile Val Ser Ile Glu Asp Pro Leu Gln Glu Asp
        275              280             285

Asp Trp Glu Gly Tyr Thr Asn Leu Thr Ala Thr Ile Gly Asp Lys Val
        290              295             300

Gln Ile Val Gly Asp Asp Phe Phe Val Thr Asn Pro Glu Arg Leu Lys
305               310              315          320

Glu Gly Ile Ala Lys Lys Ala Ala Asn Ser Ile Leu Val Lys Val Asn
        325              330             335

Gln Ile Gly Thr Leu Thr Glu Thr Phe Asp Ala Val Asp Met Ala His
        340              345             350

Arg Ala Gly Tyr Thr Ser Met Met Ser His Arg Ser Gly Glu Thr Glu
        355              360             365

Asp Thr Thr Ile Ala Asp Leu Ala Val Ala Leu Asn Cys Gly Gln Ile
        370              375             380

Lys Thr Gly Ala Pro Ala Arg Ser Asp Arg Val Ala Lys Tyr Asn Gln
385               390              395          400

Leu Leu Arg Ile Glu Gln Leu Leu Gly Asp Ala Gly Val Tyr Ala Gly
        405              410             415

Arg Ser Ala Phe Pro Arg Phe Gln Gly
        420              425

<210> SEQ ID NO 18
<211> LENGTH: 1278
<212> TYPE: DNA
<213> ORGANISM: Corynebacterium glutamicum

<400> SEQUENCE: 18

```
gtggctgaaa tcatgcacgt attcgctcgc gaaattctcg actcccgcgg taacccaacc      60
gtcgaggcag aggttttcct ggatgacggt tcccacggtg tcgcaggtgt tccatccggc     120
gcatccaccg cgtccacga ggctcatgag ctgcgtgacg gtggcgatcg ctacctgggc     180
aagggcgttt tgaaggcagt tgaaaacgtc aacgaagaaa tcggcgacga gctcgctggc     240
```

```
ctagaggctg acgatcagcg cctcatcgac gaagcaatga tcaagcttga tggcaccgcc    300
aacaagtccc gcctgggtgc aaacgcaatc cttggtgttt ccatggctgt tgcaaaggct    360
gctgctgatt ccgcaggcct cccactgttc cgctacatcg gtggaccaaa cgcacacgtt    420
cttccagttc caatgatgaa catcatcaac ggtggcgctc acgctgactc cggtgttgac    480
gttcaggaat tcatgatcgc tccaatcggt gcagagacct tctctgaggc tctccgcaac    540
ggcgcggagg tctaccacgc actgaagtcc gtcatcaagg aaaagggcct gtccaccgga    600
cttggcgatg agggcggctt cgctccttcc gtcggctcca cccgtgaggc tcttgacctt    660
atcgttgagg caatcgagaa ggctggcttc accccaggca aggacatcgc tcttgctctg    720
gacgttgctt cctctgagtt cttcaaggac ggcacctacc acttcgaagg tggccagcac    780
tccgcagctg agatggcaaa cgtttacgct gagctcgttg acgcgtaccc aatcgtctcc    840
atcgaggacc cactgcagga agatgactgg gagggttaca ccaacctcac cgcaaccatc    900
ggcgacaagg ttcagatcgt tggcgacgac ttcttcgtca ccaaccctga gcgcctgaag    960
gagggcatcg ctaagaaggc tgccaactcc atcctggtta aggtgaacca gatcggtacc   1020
ctcaccgaga ccttcgacgc tgtcgacatg gctcaccgcg caggctacac ctccatgatg   1080
tcccaccgtt ccggtgagac cgaggacacc accattgctg acctcgcagt tgcactcaac   1140
tgtggccaga tcaagactgg tgctccagca cgttccgacc gtgtcgcaaa gtacaaccag   1200
cttctccgca tcgagcagct gcttggcgac gccggcgtct acgcaggtcg cagcgcattc   1260
ccacgctttc agggctaa                                                  1278

<210> SEQ ID NO 19
<211> LENGTH: 471
<212> TYPE: PRT
<213> ORGANISM: Escherichia coli

<400> SEQUENCE: 19

Met Lys Gln Ser Thr Ile Ala Leu Ala Leu Leu Pro Leu Leu Phe Thr
 1               5                  10                  15

Pro Val Thr Lys Ala Arg Thr Pro Glu Met Pro Val Leu Glu Asn Arg
            20                  25                  30

Ala Ala Gln Gly Asp Ile Thr Ala Pro Gly Gly Ala Arg Arg Leu Thr
        35                  40                  45

Gly Asp Gln Thr Ala Ala Leu Arg Asp Ser Leu Ser Asp Lys Pro Ala
    50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
        115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
            180                 185                 190
```

Pro Ser Ala Thr Ser Glu Lys Cys Pro Gly Asn Ala Leu Glu Lys Gly
        195                 200                 205

Gly Lys Gly Ser Ile Thr Glu Gln Leu Leu Asn Ala Arg Ala Asp Val
        210                 215                 220

Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
            260                 265                 270

Gln Gln Lys Pro Leu Leu Gly Leu Phe Ala Asp Gly Asn Met Pro Val
        275                 280                 285

Arg Trp Leu Gly Pro Lys Ala Thr Tyr His Gly Asn Ile Asp Lys Pro
    290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
            340                 345                 350

His Ala Ala Asn Pro Cys Gly Gln Ile Gly Glu Thr Val Asp Leu Asp
        355                 360                 365

Glu Ala Val Gln Arg Ala Leu Glu Phe Ala Lys Lys Glu Gly Asn Thr
    370                 375                 380

Leu Val Ile Val Thr Ala Asp His Ala His Ala Ser Gln Ile Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
            420                 425                 430

Glu His Thr Gly Ser Gln Leu Arg Ile Ala Ala Tyr Gly Pro His Ala
        435                 440                 445

Ala Asn Val Val Gly Leu Thr Asp Gln Thr Asp Leu Phe Tyr Thr Met
    450                 455                 460

Lys Ala Ala Leu Gly Leu Lys
465                 470

<210> SEQ ID NO 20
<211> LENGTH: 1416
<212> TYPE: DNA
<213> ORGANISM: Escherichia coli

<400> SEQUENCE: 20
gtgaaacaaa gcactattgc actggcactc ttaccgttac tgtttacccc tgtgacaaaa      60
gcccggacac cagaaatgcc tgttctggaa accgggctg ctcagggcga tattactgca     120
cccggcggtg ctcgccgttt aacgggtgat cagactgccg ctctgcgtga ttctcttagc     180
gataaacctg caaaaaatat tattttgctg attggcgatg ggatggggga ctcggaaatt     240
actgccgcac gtaattatgc cgaaggtgcg ggcggctttt ttaaaggtat agatgcctta     300
ccgcttaccg ggcaatacac tcactatgcg ctgaataaaa aaaccggcaa accgactac     360 gtcaccgact cggctgcatc agcaaccgcc tggtcaaccg gtgtcaaaac ctataacggc     420
gcgctgggcg tcgatattca cgaaaaagat cacccaacga ttctggaaat ggcaaaagcc     480
gcaggtctgg cgaccggtaa cgtttctacc gcagagttgc aggatgccac gccgctgcg     540

```
ctggtggcac atgtgacctc gcgcaaatgc tacggtccga gcgcgaccag tgaaaaatgt      600
ccgggtaacg ctctggaaaa aggcggaaaa ggatcgatta ccgaacagct gcttaacgct      660
cgtgccgacg ttacgcttgg cggcggcgca aaacctttg ctgaaacggc aaccgctggt       720
gaatggcagg gaaaaacgct gcgtgaacag gcacaggcgc gtggttatca gttggtgagc      780
gatgctgcct cactgaattc ggtgacggaa gcgaatcagc aaaaacccct gcttggcctg      840
tttgctgacg gcaatatgcc agtgcgctgg ctaggaccga agcaacgta ccatggcaat       900 atcgataagc ccgcagtcac ctgtacgcca atccgcaac gtaatgacag tgtaccaacc       960
ctggcgcaga tgaccgacaa agccattgaa ttgttgagta aaatgagaa aggctttttc     1020 ctgcaagttg aaggtgcgtc aatcgataaa caggatcatg ctgcgaatcc ttgtgggcaa     1080
attggcgaga cggtcgatct cgatgaagcc gtacaacggg cgctggaatt cgctaaaaag     1140
gagggtaaca cgctggtcat agtcaccgct gatcacgccc acgccagcca gattgttgcg     1200
ccggatacca aagctccggg cctcacccag gcgctaaata ccaaagatgg cgcagtgatg     1260
gtgatgagtt acgggaactc cgaagaggat tcacaagaac ataccggcag tcagttgcgt     1320
attgcggcgt atggcccgca tgccgccaat gttgttggac tgaccgacca gaccgatctc     1380
ttctacacca tgaaagccgc tctggggctg aaataa                               1416
```

<210> SEQ ID NO 21
<211> LENGTH: 375
<212> TYPE: PRT
<213> ORGANISM: Mus musculus

<400> SEQUENCE: 21

```
Met Glu Glu Glu Ile Ala Ala Leu Val Ile Asp Asn Gly Ser Gly Met
  1               5                  10                  15

Cys Lys Ala Gly Phe Ala Gly Asp Asp Ala Pro Arg Ala Val Phe Pro
             20                  25                  30

Ser Ile Val Gly Arg Pro Arg His Gln Gly Val Met Val Gly Met Gly
         35                  40                  45

Gln Lys Asp Ser Tyr Val Gly Asp Glu Ala Gln Ser Lys Arg Gly Ile
     50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
                 85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220
```

```
Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
            245                 250                 255

Cys Pro Glu Ala Leu Phe Gln Pro Ser Phe Leu Gly Met Glu Ser Cys
        260                 265                 270

Gly Ile His Glu Thr Thr Phe Asn Ser Ile Met Lys Cys Asp Val Asp
    275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
            325                 330                 335

Tyr Ser Val Trp Ile Gly Gly Ser Ile Leu Ala Ser Leu Ser Thr Phe
        340                 345                 350

Gln Gln Met Trp Ile Ser Lys Gln Glu Tyr Asp Glu Ser Gly Pro Ser
    355                 360                 365

Ile Val His Arg Lys Cys Phe
    370                 375

<210> SEQ ID NO 22
<211> LENGTH: 1128
<212> TYPE: DNA
<213> ORGANISM: Mus musculus

<400> SEQUENCE: 22
atggaagaag aaatcgccgc actcgtcatt gacaatggct ccggcatgtg caaagccggc      60
tttgctggcg acgacgcccc cagggccgtg ttcccttcca tcgtagggcg ccccgacac     120
cagggcgtca tggtgggcat gggccagaaa gactcatacg tgggtgacga ggcccagagc     180
aagaggggta tcctgaccct gaagtaccct atcgaacacg gcattgtcac taactgggac     240
gacatggaga gatctggca ccacaccttc tacaatgagc tgcgtgtggc tcctgaggag     300
cacccggtgc ttctgaccga ggccccctg aaccccaaag ctaacagaga aagatgacg     360
cagataatgt ttgaaacctt caataccca gccatgtacg tggccattca ggcggtgctg     420
tccttgtatg catctgggcg caccactggc attgtcatgg actctggtga cggggtcaca     480
cacacagtgc ccatctatga gggctacgcc cttccccacg ccatcttgcg tctggacctg     540
gctggccggg aactgacaga ctacctcatg aagatcctga ctgaacgggg ctacagcttt     600
accaccactg ctgagaggga aattgttcgt gacataaagg agaagctgtg ctatgttgcc     660
ctggattttg agcaagaaat ggctactgct gcatcatctt cctccttgga aagagttac     720
gagctgcccg acgggcaggt gatcaccatt ggcaatgagc ggttccggtg tccggaggca     780
ctcttccagc cttccttcct gggcatggag tcctgtggta tccatgagac cactttcaac     840
tccatcatga gtgtgatgt ggatatccgc aaagacctgt atgccaatac agtgctgtct     900
ggtggtacca ccatgtaccc aggcattgct gacaggatgc agaaggagat cacagcccta     960
gcacctagca cgatgaagat taagatcatt gctccccctg agcgcaagta ctcagtctgg    1020
atcggtggct ccattctggc ctcactgtcc accttccagc agatgtggat cagcaagcag    1080
gagtatgatg agtcaggccc ctccatcgtc caccgcaaat gcttctag                 1128

<210> SEQ ID NO 23
<211> LENGTH: 375
```

```
<212> TYPE: PRT
<213> ORGANISM: Mus musculus

<400> SEQUENCE: 23

Met Asp Asp Ile Ala Ala Leu Val Val Asp Asn Gly Ser Gly Met
 1               5                  10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
370                 375

<210> SEQ ID NO 24
<211> LENGTH: 1128
```

```
<212> TYPE: DNA
<213> ORGANISM: Mus musculus

<400> SEQUENCE: 24
atggatgacg atatcgctgc gctggtcgtc gacaacggct ccggcatgtg caaagccggc        60
ttcgcgggcg acgatgctcc ccgggctgta ttcccctcca tcgtgggccg ccctaggcac       120
cagggtgtga tggtgggaat gggtcagaag gactcctatg tgggtgacga ggcccagagc       180
aagagaggta tcctgaccct gaagtacccc attgaacatg gcattgttac caactgggac       240
gacatggaga gatctggcca ccacaccttc tacaatgagc tgcgtgtggc ccctgaggag       300
caccctgtgc tgctcaccga gccccctg aaccctaagg ccaaccgtga aaagatgacc       360
cagatcatgt ttgagacctt caacacccca gccatgtacg tagccatcca ggctgtgctg       420
tccctgtatg cctctggtcg taccacaggc attgtgatgg actccggaga cggggtcacc       480
cacactgtgc ccatctacga gggctatgct ctccctcacg ccatcctgcg tctggacctg       540
gctggccggg acctgacaga ctacctcatg aagatcctga ccgagcgtgg ctacagcttc       600
accaccacag ctgagaggga atcgtgcgt gacatcaaag agaagctgtg ctatgttgct       660
ctagacttcg agcaggagat ggccactgcc gcatcctctt cctccctgga aagagctat       720 gagctgcctg acggccaggt catcactatt ggcaacgagc ggttccgatg ccctgaggct       780
cttttccagc cttccttctt gggtatgaa tcctgtggca tccatgaaac tacattcaat       840
tccatcatga agtgtgacgt tgacatccgt aaagacctct atgccaacac agtgctgtct       900
ggtggtacca ccatgtaccc aggcattgct gacaggatgc agaaggagat tactgctctg       960
gctcctagca ccatgaagat caagatcatt gctcctcctg agcgcaagta ctctgtgtgg      1020
atcggtggct ccatcctggc ctcactgtcc accttccagc agatgtggat cagcaagcag      1080
gagtacgatg agtccggccc ctccatcgtg caccgcaagt gcttctag                  1128

<210> SEQ ID NO 25
<211> LENGTH: 97
<212> TYPE: PRT
<213> ORGANISM: Thermus thermophilus

<400> SEQUENCE: 25

Met Ala Ala Lys Lys Thr Val Thr Lys Ala Asp Leu Val Asp Gln Val
1               5                   10                  15

Ala Gln Ala Thr Gly Leu Lys Lys Lys Asp Val Lys Ala Met Val Asp
            20                  25                  30

Ala Leu Leu Ala Lys Val Glu Glu Ala Leu Ala Asn Gly Ser Lys Val
        35                  40                  45

Gln Leu Thr Gly Phe Gly Thr Phe Glu Val Arg Lys Arg Lys Ala Arg
    50                  55                  60

Thr Gly Val Lys Pro Gly Thr Lys Glu Lys Ile Lys Ile Pro Ala Thr
65                  70                  75                  80

Gln Tyr Pro Ala Phe Lys Pro Gly Lys Ala Leu Lys Asp Lys Val Lys
                85                  90                  95

Lys

<210> SEQ ID NO 26
<211> LENGTH: 294
<212> TYPE: DNA
<213> ORGANISM: Thermus thermophilus

<400> SEQUENCE: 26
atggctgcga agaagacggt gaccaaagcg gatctggtgg accaggtggc ccaggccacc        60
```

```
gggctcaaga agaaggacgt gaaggccatg gtggacgccc tgctggccaa ggtggaggag      120
gccttggcca acgggagcaa ggtccagctc acgggcttcg gcacctttga ggtgcgcaag      180
cgcaaggccc gcaccggggt gaagccgggc accaaggaga agatcaagat ccccgccacc      240
cagtatcccg ccttcaagcc cggcaaggcc ctgaaggata aggtcaagaa gtaa            294
```

<210> SEQ ID NO 27
<211> LENGTH: 375
<212> TYPE: PRT
<213> ORGANISM: Homo sapiens

<400> SEQUENCE: 27

```
Met Glu Glu Glu Ile Ala Ala Leu Val Ile Asp Asn Gly Ser Gly Met
 1               5                  10                  15

Cys Lys Ala Gly Phe Ala Gly Asp Asp Ala Pro Arg Ala Val Phe Pro
             20                  25                  30

Ser Ile Val Gly Arg Pro Arg His Gln Gly Val Met Val Gly Met Gly
         35                  40                  45

Gln Lys Asp Ser Tyr Val Gly Asp Glu Ala Gln Ser Lys Arg Gly Ile
     50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
                 85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335
```

```
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
        355                 360                 365
Ile Val His Arg Lys Cys Phe
        370                 375

<210> SEQ ID NO 28
<211> LENGTH: 1128
<212> TYPE: DNA
<213> ORGANISM: Homo sapiens

<400> SEQUENCE: 28
atggaagaag agatcgccgc gctggtcatt gacaatggct ccggcatgtg caaagctggt      60
tttgctgggg acgacgctcc ccgagccgtg tttccttcca tcgtcgggcg ccccagacac     120
cagggcgtca tggtgggcat gggccagaag gactcctacg tgggcgacga ggcccagagc     180
aagcgtggca tcctgaccct gaagtacccc attgagcatg gcatcgtcac caactgggac     240
gacatggaga gatctggcca ccacccttc tacaacgagc tgcgcgtggc cccggaggag     300
cacccagtgc tgctgaccga ggccccctg aaccccaagg ccaacagaga gaagatgact     360
cagattatgt ttgagacctt caacaccccg ccatgtacg tggccatcca ggccgtgctg     420
tccctctacg cctctgggcg caccactggc attgtcatgg actctggaga cggggtcacc     480
cacacggtgc ccatctacga gggctacgcc ctcccccacg ccatcctgcg tctggacctg     540
gctggccggg acctgaccga ctacctcatg aagatcctca ctgagcgagg ctacagcttc     600
accaccacgg ccgagcggga aatcgtgcgc gacatcaagg agaagctgtg ctacgtcgcc     660
ctggacttcg agcaggagat ggccaccgcc gcatcctcct cttctctgga aagagctac     720
gagctgcccg atggccaggt catcaccatt ggcaatgagc ggttccggtg tccggaggcg     780
ctgttccagc cttccttcct gggtatggaa tcttgcggca tccacgagac caccttcaac     840
tccatcatga gtgtgacgt ggacatccgc aaagacctgt acgccaacac ggtgctgtcg     900
ggcggcacca ccatgtaccc gggcattgcc gacaggatgc agaaggagat caccgccctg     960
gcgcccagca ccatgaagat caagatcatc gcaccccag agcgcaagta tcggtgtgg    1020
atcggtggct ccatcctggc ctcactgtcc accttccagc agatgtggat tagcaagcag    1080
gagtacgacg agtcgggccc ctccatcgtc accgcaaat gcttctaa                 1128

<210> SEQ ID NO 29
<211> LENGTH: 375
<212> TYPE: PRT
<213> ORGANISM: Homo sapiens

<400> SEQUENCE: 29

Met Asp Asp Asp Ile Ala Ala Leu Val Val Asp Asn Gly Ser Gly Met
  1               5                  10                  15
Cys Lys Ala Gly Phe Ala Gly Asp Asp Ala Pro Arg Ala Val Phe Pro
             20                  25                  30
Ser Ile Val Gly Arg Pro Arg His Gln Gly Val Met Val Gly Met Gly
         35                  40                  45
Gln Lys Asp Ser Tyr Val Gly Asp Glu Ala Gln Ser Lys Arg Gly Ile
     50                  55                  60
Leu Thr Leu Lys Tyr Pro Ile Glu His Gly Ile Val Thr Asn Trp Asp
 65                  70                  75                  80
Asp Met Glu Lys Ile Trp His His Thr Phe Tyr Asn Glu Leu Arg Val
                 85                  90                  95
```

```
Ala Pro Glu Glu His Pro Val Leu Leu Thr Glu Ala Pro Leu Asn Pro
            100                 105                 110
Lys Ala Asn Arg Glu Lys Met Thr Gln Ile Met Phe Glu Thr Phe Asn
        115                 120                 125
Thr Pro Ala Met Tyr Val Ala Ile Gln Ala Val Leu Ser Leu Tyr Ala
    130                 135                 140
Ser Gly Arg Thr Thr Gly Ile Val Met Asp Ser Gly Asp Gly Val Thr
145                 150                 155                 160
His Thr Val Pro Ile Tyr Glu Gly Tyr Ala Leu Pro His Ala Ile Leu
                165                 170                 175
Arg Leu Asp Leu Ala Gly Arg Asp Leu Thr Asp Tyr Leu Met Lys Ile
            180                 185                 190
Leu Thr Glu Arg Gly Tyr Ser Phe Thr Thr Thr Ala Glu Arg Glu Ile
        195                 200                 205
Val Arg Asp Ile Lys Glu Lys Leu Cys Tyr Val Ala Leu Asp Phe Glu
    210                 215                 220
Gln Glu Met Ala Thr Ala Ala Ser Ser Ser Ser Leu Glu Lys Ser Tyr
225                 230                 235                 240
Glu Leu Pro Asp Gly Gln Val Ile Thr Ile Gly Asn Glu Arg Phe Arg
                245                 250                 255
Cys Pro Glu Ala Leu Phe Gln Pro Ser Phe Leu Gly Met Glu Ser Cys
            260                 265                 270
Gly Ile His Glu Thr Thr Phe Asn Ser Ile Met Lys Cys Asp Val Asp
        275                 280                 285
Ile Arg Lys Asp Leu Tyr Ala Asn Thr Val Leu Ser Gly Gly Thr Thr
    290                 295                 300
Met Tyr Pro Gly Ile Ala Asp Arg Met Gln Lys Glu Ile Thr Ala Leu
305                 310                 315                 320
Ala Pro Ser Thr Met Lys Ile Lys Ile Ile Ala Pro Pro Glu Arg Lys
                325                 330                 335
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
        355                 360                 365
Ile Val His Arg Lys Cys Phe
    370                 375

<210> SEQ ID NO 30
<211> LENGTH: 1128
<212> TYPE: DNA
<213> ORGANISM: Homo sapiens

<400> SEQUENCE: 30
atggaagaag agatcgccgc gctggtcatt gacaatggct ccggcatgtg caaagctggt      60
tttgctgggg acgacgctcc ccgagccgtg tttccttcca tcgtcgggcg ccccagacac     120
cagggcgtca tggtgggcat gggccagaag gactcctacg tgggcgacga ggcccagagc     180
aagcgtggca tcctgaccct gaagtacccc attgagcatg gcatcgtcac caactgggac     240
gacatggaga agatctggca ccacaccttc tacaacgagc tgcgcgtggc cccggaggag     300
cacccagtgc tgctgaccga gccccccctg aaccccaagg ccaacagaga gaagatgact     360
cagattatgt ttgagacctt caacaccccg gccatgtacg tggccatcca ggccgtgctg     420
tccctctacg cctctgggcg caccactggc attgtcatgg actctggaga cggggtcacc     480
cacacggtgc ccatctacga gggctacgcc ctcccccacg ccatcctgcg tctggacctg     540
```

```
gctggccggg acctgaccga ctacctcatg aagatcctca ctgagcgagg ctacagcttc    600
accaccacgg ccgagcggga atcgtgcgc gacatcaagg agaagctgtg ctacgtcgcc     660
ctggacttcg agcaggagat ggccaccgcc gcatcctcct cttctctgga gaagagctac    720
gagctgcccg atggccaggt catcaccatt ggcaatgagc ggttccggtg tccggaggcg    780
ctgttccagc cttccttcct gggtatgaa tcttgcggca tccacgagac cacctttcaac    840 tccatcatga agtgtgacgt ggacatccgc aaagacctgt acgccaacac ggtgctgtcg    900
ggcggcacca ccatgtaccc gggcattgcc gacaggatgc agaaggagat caccgccctg    960
gcgcccagca ccatgaagat caagatcatc gcacccccag agcgcaagta ctcggtgtgg   1020
atcggtggct ccatcctggc ctcactgtcc accttccagc agatgtggat tagcaagcag   1080
gagtacgacg agtcgggccc ctccatcgtc caccgcaaat gcttctaa              1128
```

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 31
gttaagcttc ggacaccaga aatgcctgt                                      29

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 32
gttgcggccg ctttcagccc cagagcggct                                     30

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 33
ggaattcgct agcatgcaag aagggcaaaa ccg                                 33

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 34
gttggatccc cgccagccat ctgttttttcg c                                  31

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:Artificially

```
                Synthesized Primer Sequence

<400> SEQUENCE: 35
ggaattccat atggctgcga agaagacggt                                    30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 36
gttggatccc ccttcttgac cttatccttc                                    30

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 37
agaaaagctt agtaaaggag aagaactttt cact                               34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 38
tcatgcggcc gcaagctcat ccatgccatg tgta                               34
```